US012653624B2

(12) United States Patent (10) Patent No.: US 12,653,624 B2
Polonsky et al. (45) Date of Patent: Jun. 16, 2026

(54) INSTRUMENT PRESENCE AND ROTATIONAL OFFSET SENSING IN FLEXIBLE SYSTEM

(71) Applicant: Intuitive Surgical Operations, Inc., Sunnyvale, CA (US)

(72) Inventors: Andrey Polonsky, Sunnyvale, CA (US); David W. Bailey, Sunnyvale, CA (US); Adam K. Begley, Sunnyvale, CA (US); Joseph D. Bogusky, Sunnyvale, CA (US); Dominique D. Brichard, Sunnyvale, CA (US); Lucas S. Gordon, Sunnyvale, CA (US); Tajalli Shoghi Ghalehshahi, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 194 days.

(21) Appl. No.: 18/243,773

(22) Filed: Sep. 8, 2023

(65) Prior Publication Data

US 2024/0081915 A1     Mar. 14, 2024

Related U.S. Application Data

(60) Provisional application No. 63/405,095, filed on Sep. 9, 2022.

(51) Int. Cl.
A61B 34/20     (2016.01)
G01R 33/07     (2006.01)

(52) U.S. Cl.
CPC ............ A61B 34/20 (2016.02); G01R 33/072 (2013.01); *A61B 2034/2051* (2016.02); *A61B 2034/2072* (2016.02); *A61B 2034/2074* (2016.02)

(58) Field of Classification Search
CPC ............ A61B 34/20; A61B 2034/2051; A61B 2034/2072; A61B 2034/2074;
(Continued)

(56) References Cited

U.S. PATENT DOCUMENTS 7,686,767 B2 *   3/2010   Maschke ................ A61B 34/70
                                                                 600/435
2013/0096572 A1 *   4/2013   Donhowe .............. A61B 34/10
                                                                 606/130
(Continued)

OTHER PUBLICATIONS

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Joel Lamprecht
(74) *Attorney, Agent, or Firm* — Osha Bergman Watanabe & Burton LLP

(57)     ABSTRACT

A medical system may include an elongated flexible body including a channel extending through the elongated flexible body. The elongated flexible body includes an articulable portion extending along at least a portion of a length of the elongated flexible body. The medical system may include an instrument configured to be received in the channel of the elongated flexible body, a magnetic field generator configured to generate a magnetic field within the channel, and a magnetic field sensor configured to detect the magnetic field generated by the magnetic field generator.

18 Claims, 14 Drawing Sheets

(58) Field of Classification Search
CPC ...... A61B 2034/105; A61B 2034/2059; A61B
2034/2061; A61B 2034/301; A61B
17/00234; A61B 2017/003; A61B
2017/00305; A61B 2017/00318; G01R
33/072
See application file for complete search history.

(56) References Cited

U.S. PATENT DOCUMENTS

2015/0038788 A1* 2/2015 Ohline ................... A61B 5/068
600/117
2017/0367767 A1* 12/2017 Blumenkranz ........ A61B 34/20

* cited by examiner

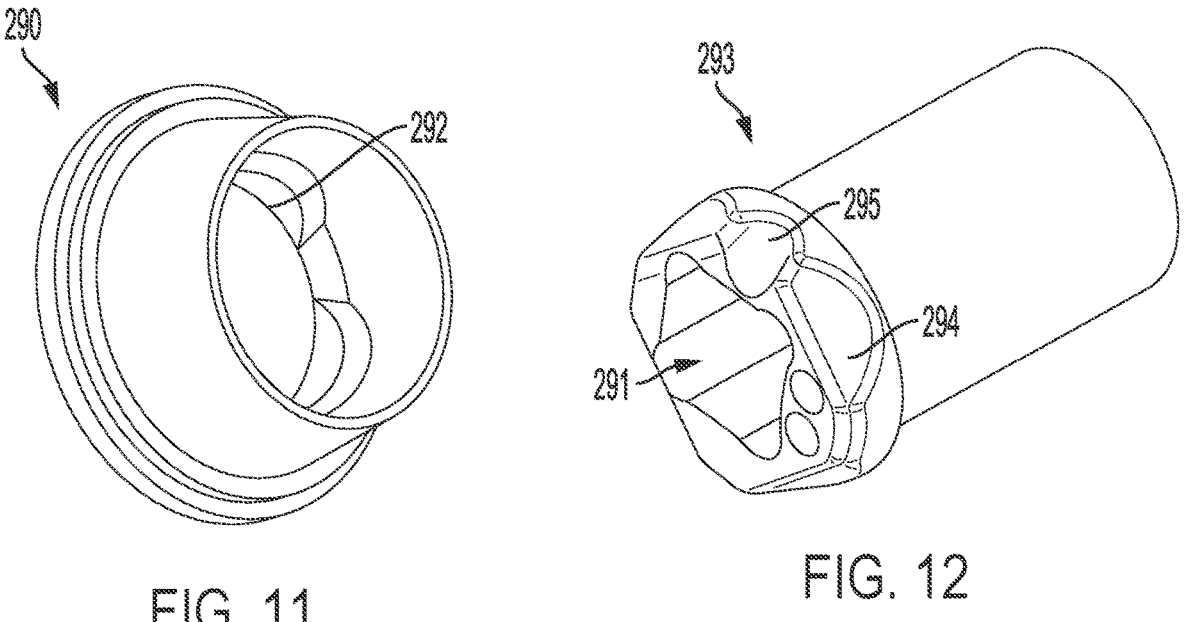
FIG. 11
FIG. 12
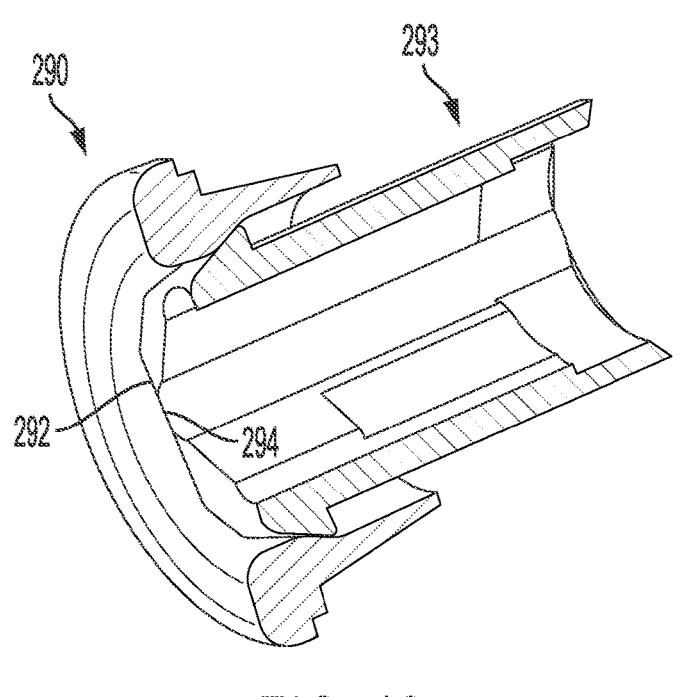
FIG. 13

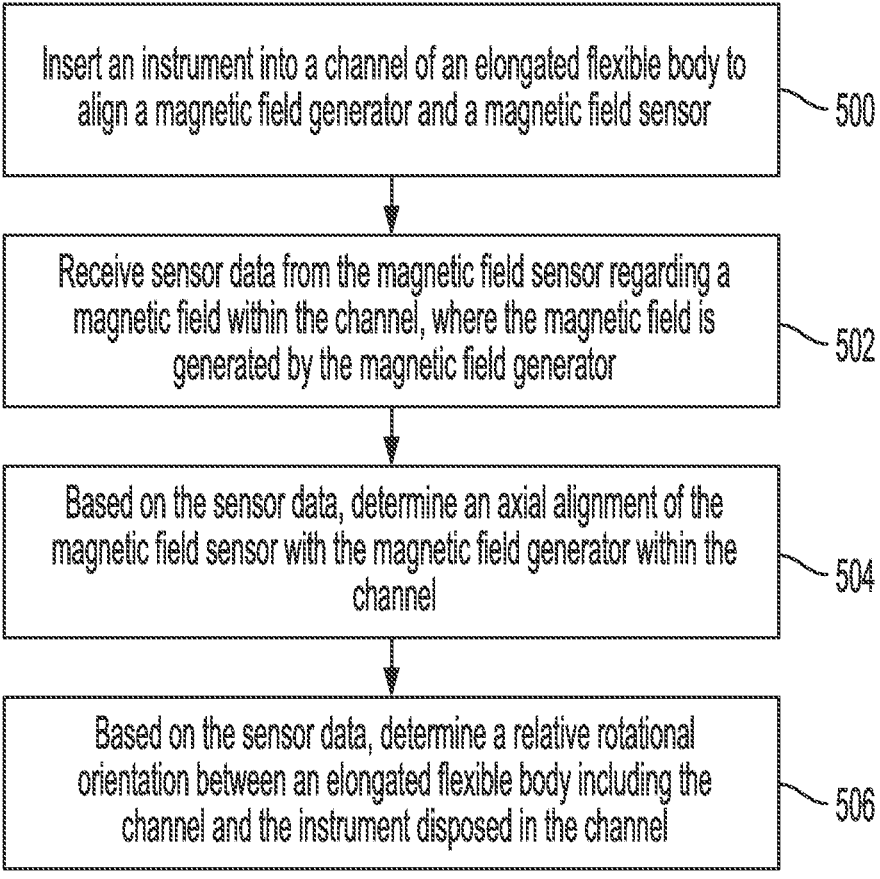

Insert an instrument into a channel of an elongated flexible body to align a magnetic field generator and a magnetic field sensor — 500

Receive sensor data from the magnetic field sensor regarding a magnetic field within the channel, where the magnetic field is generated by the magnetic field generator — 502

Based on the sensor data, determine an axial alignment of the magnetic field sensor with the magnetic field generator within the channel — 504

Based on the sensor data, determine a relative rotational orientation between an elongated flexible body including the channel and the instrument disposed in the channel — 506

FIG. 17

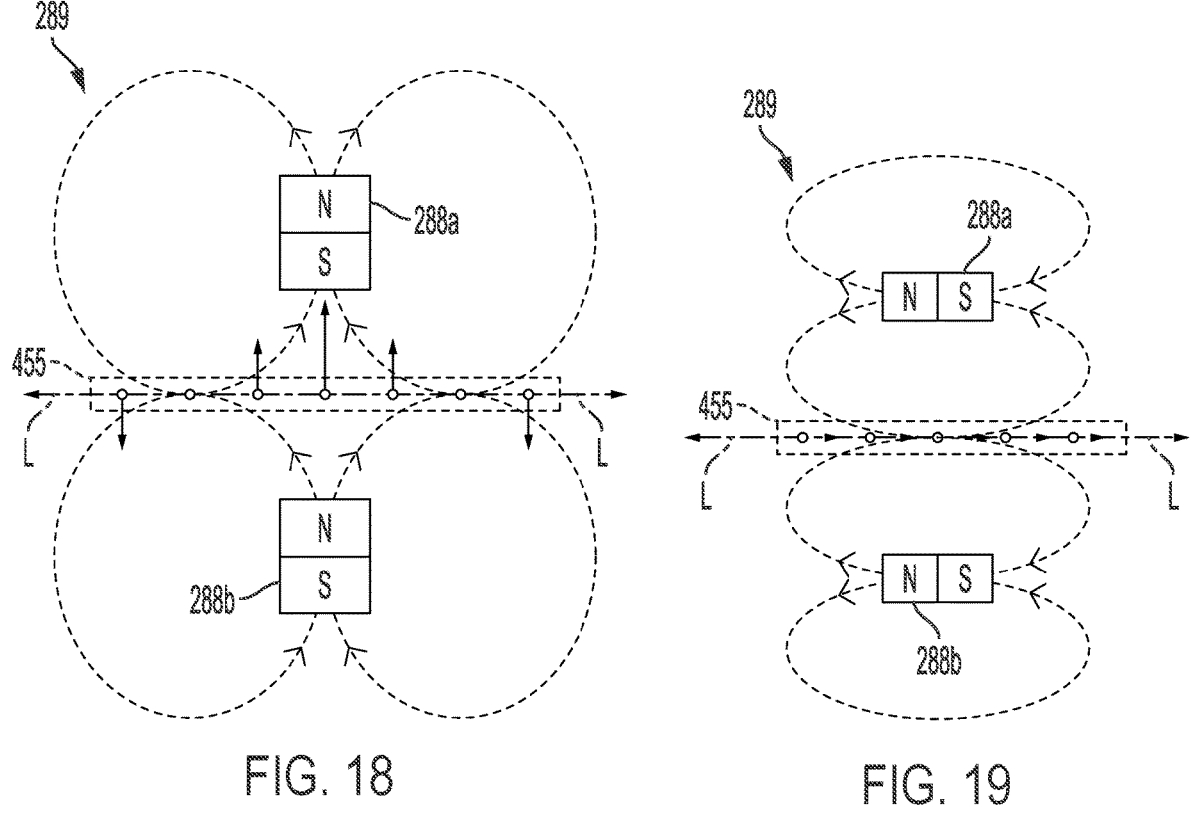
FIG. 18                    FIG. 19

INSTRUMENT PRESENCE AND ROTATIONAL OFFSET SENSING IN FLEXIBLE SYSTEM

CROSS-REFERENCE TO RELATED APPLICATIONS

This application claims the benefit of priority under 35 U S.C. § 119(e) to U.S. Provisional Patent Application Ser. No. 63/405,095, filed on Sep. 9, 2022, which is hereby incorporated by reference herein in its entirety.

FIELD

Disclosed embodiments are related to instrument presence, axial offset, and rotational offset sensing in flexible systems and related methods of use.

BACKGROUND

Minimally invasive medical techniques are intended to reduce the amount of tissue that is damaged during medical procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. To assist with reaching the target tissue location, the location and movement of the medical instruments may be correlated with pre-operative or intra-operative images of the patient anatomy. With the image-guided instruments correlated to the images, the instruments may navigate natural or surgically created passageways in anatomic systems such as the lungs, the colon, the intestines, the kidneys, the heart, the circulatory system, or the like.

SUMMARY

In some embodiments, a medical system includes an elongated flexible body including a channel extending through the elongated flexible body, where the elongated flexible body includes an articulable portion extending along at least a portion of a length of the elongated flexible body. The medical system also includes an instrument configured to be received in the channel of the elongated flexible body, a magnetic field generator configured to generate a magnetic field within the channel, a magnetic field sensor configured to detect the magnetic field generated by the magnetic field generator, and a controller comprising at least one processor. The controller is configured to receive sensor data from the magnetic field sensor regarding the magnetic field generated by the magnetic field generator, and based on the sensor data, determine a relative rotational orientation between the instrument and the elongated flexible body.

In some embodiments, a method of operating a medical system includes the following. The medical system comprises an elongated flexible body including a channel extending through the elongated flexible body, where the elongated flexible body includes an articulable portion extending along at least a portion of a length of the elongated flexible body, and an instrument configured to be received in the channel of the elongated flexible body. The method comprises receiving sensor data from a magnetic field sensor regarding a magnetic field within the channel, where the magnetic field is generated by a magnetic field generator. The method also comprises, based on the sensor data, determining a relative rotational orientation between the elongated flexible body and the instrument.

In some embodiments, a non-transitory computer-readable storage medium stores instructions that, when executed by at least one processor associated with a computer-assisted device, causes the at least one processor to perform a method. The method comprises receiving sensor data from a magnetic field sensor regarding a magnetic field within the channel, where the magnetic field is generated by a magnetic field generator. The method also comprises, based on the sensor data, determining a relative rotational orientation between an elongated flexible body and an instrument.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 11 illustrates a perspective view of a tip cap for a flexible elongate device, in accordance with embodiments of the present disclosure;

FIG. 12 illustrates a perspective view of an instrument housing for use with a flexible elongate device, in accordance with embodiments of the present disclosure;

FIG. 13 illustrates the tip cap of FIG. 11 in use with the instrument housing of FIG. 12;

FIG. 17 is a flow chart for an embodiment of operating a medical system comprising a flexible elongate device;

FIG. 18 illustrates a magnetic field generated by a magnetic field generator in accordance with another embodiment;

FIG. 19 illustrates a magnetic field generated by a magnetic field generator in accordance with another embodiment;

DETAILED DESCRIPTION

Figure 1:
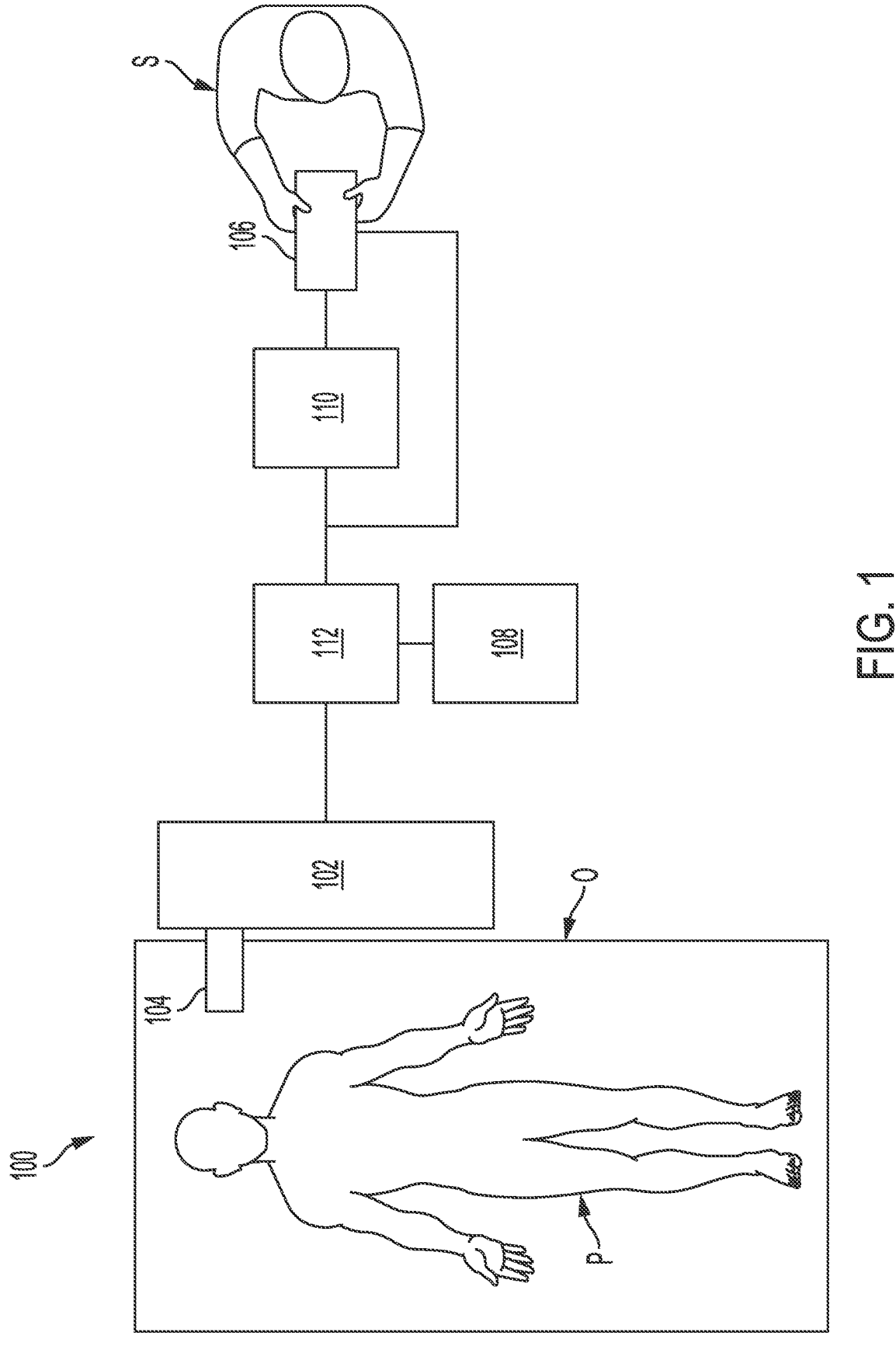
FIG. 1 illustrates a computer-assisted system, in accordance with embodiments of the present disclosure.

Embodiments relate to a flexible computer-assisted system (e.g., a robotic system) that uses an instrument tracking and referencing system to operate within a known three-dimensional space. The tracking may operate in various ways. For example, control of one or more actuators of a flexible computer-assisted system may allow the flexible computer assisted system to maintain knowledge of a pose, position, or orientation of one or more portions of the flexible computer-assisted system (e.g., an instrument, a distal end of a flexible elongate device, etc.) as the pose changes based on the commands to the one or more actuators. In another example, a flexible computer-assisted system may employ one or more sensors (e.g., shape sensors, position sensors, ultrasound sensors, imaging sensors, etc.) that provide information regarding the pose, position, or orientation of one or more portions of the flexible computer-assisted system during operation.

During operation, an imaging probe or other photosensitive detector (also referred to as a "camera") may be employed to provide information to an operator of the flexible computer-assisted system. For example, the flexible computer-assisted system may include a flexible elongate device (e.g., a catheter) with an elongated flexible body that includes a channel through which the camera is inserted. The flexible elongate device may be steered (e.g., via actuators) through anatomical passageways to a target tissue using images captured by the camera at the distal end of the flexible elongate device for navigation. As discussed above, the pose, position, or orientation of the flexible elongate device may be tracked in various ways. The tracked pose, position, or orientation may be defined in a reference frame used by the flexible computer-assisted system. However, a rotational orientation of the camera relative to the flexible elongate device can vary depending on how the camera is inserted within the flexible elongate device. Additionally, the relative rotational orientation between the camera and flexible elongate device may change as the flexible elongate device traverses the patient anatomy. If the rotational orientation of the camera relative to the flexible elongate device is unknown or otherwise unreliable, then the images captured by the camera cannot be reliably registered to the reference frame of the flexible elongate device. This results in the images being captured being unsuitable for assisting in the navigation of the flexible elongate device.

As such, tracking the rotational orientation of the camera with respect to the reference frame of the computer-assisted system (e.g., directions of motion of the flexible computer-assisted system) is useful for computer-assisted control of the flexible elongate device. For example, if the reference frame of the camera is not registered to the reference frame of the flexible computer-assisted system, the navigation feedback provided to an operator may be disorienting as the features captured in the image feed move counterintuitively with respect to the inputs provided to move the flexible elongate device. Additionally, in some embodiments, detecting the presence of any instrument with respect to a distal portion of a flexible elongate device may be important for computer-assisted control of the instrument, such as by allowing the flexible computer-assisted system to detect proper insertion of the desired instrument within the channel of the flexible elongate device.

In some embodiments, determining an axial position (e.g., axial offset) of an instrument with respect to a distal portion of a flexible elongate device may be important for computer-assisted control of the instrument. The determined axial position may be used to control advancement or retraction of the instrument with respect to the flexible elongate device. Determining an axial position may allow the flexible computer-assisted system to determine the physical characteristics of the flexible elongated device with respect to the instrument received (e.g., how far the instrument protrudes past the distal portion of the flexible elongate device). Additionally, determining an axial position may have benefits including confidence in location of the instrument and sample quality from the instrument. For example, axial position determination for forceps may allow for a determination of whether the forceps are adequately outside the distal portion to open properly and/or whether the forceps retracted into the distal portion while closing, which may increase the likelihood of a failure to obtain a sample. As another example, determination of an axial position of the instrument may be used to ensure that an energized instrument, such as an ablation probe or electroporation probe, has been sufficiently advanced beyond the distal tip of the flexible elongate device prior to activation for treatment. As another example, in some embodiments axial position determination may allow for a more accurate recording of where a sample is taken during a biopsy (e.g., with forceps, needles, or brushes). As still another example, in some embodiments, axial position determination may allow for more accurate recording of where something was imaged within the body with an instrument (e.g., radial endobronchial ultrasound rEBUS).

In some embodiments, a flexible elongate device (which includes an elongated flexible body) and an instrument may include a magnetic field generator and a magnetic field sensor. The magnetic field sensor may be configured to determine a presence, position, and orientation of a magnetic field generated by the magnetic field generator. One of the magnetic field generator and magnetic field sensor may be attached to the elongated flexible body, and the other may be attached to the instrument. Accordingly, when the instrument is inserted into a channel of the elongated flexible body, the magnetic field sensor may be able to detect a presence of the instrument (e.g., via the presence of a magnetic field), a longitudinal position of the instrument in the channel (e.g., via the position of the magnetic field), and also may detect a rotational orientation of the instrument (e.g., via a directionality of the magnetic field). In this manner, the rotational orientation of the instrument with respect to a reference frame of the elongated flexible body may be determined for calibration purposes. A magnetic field generator may include one or more permanent magnets and/or electromagnets, in some embodiments. A magnetic field sensor may include a Hall effect sensor (e.g., a three-dimensional Hall effect sensor), in some embodiments. Techniques described herein may employ at least one processor configured to determine an orientation of an instrument relative to a flexible computer-assisted system reference frame based on information provided by the magnetic field sensor.

Advantageously, embodiments discussed herein provide for alignment of a reference frame of an instrument with a reference frame of a flexible computer-assisted system in a manner that simplifies and improves the use of the system. For example, when the instrument is a camera, the instrument may be inserted within the channel of the flexible elongate device at any rotational orientation. The flexible computer-assisted system can detect the rotational orientation at insertion and any changes to the rotational orientation automatically and can adjust the visual presentation of the images (e.g., the rotational orientation) captured by camera automatically to facilitate intuitive navigation control.

Embodiments discussed herein that use of magnetic field sensor and generator provide for rotational orientation determination and instrument detection in a manner that is computationally inexpensive and compatible with any type of instrument. Additionally, magnetic field sensors and generators have small form factors, and thus their use does not significantly inhibit the flexibility of a flexible computer-assisted system or substantially increase the size of the flexible computer-assisted system.

In the following detailed description, numerous specific details are set forth in order to provide a thorough understanding of the disclosed embodiments. However, one skilled in the art will appreciate that the embodiments of this disclosure may be practiced without these specific details. In other instances, well known methods, procedures, components, and circuits have not been described in detail so as not to unnecessarily obscure aspects of the embodiments. Therefore, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). Further, as used herein, the term "distal" means a location closer to a surgical or other target site and the term "proximal" means a location farther away from the surgical or other target site, unless otherwise indicated.

According to exemplary embodiments described herein, position and/or orientation may be measured and discussed with respect to a reference frame. In some cases, a reference frame may be an absolute global reference frame which does not change. For example, a local gravitational direction may establish a global reference frame relative to earth. In some cases, a reference frame may be a local reference frame tied to an orientation or position of a component of a computer-assisted system. For example, a local reference frame may be established based on a table on which a patient lies, or on the orientation of a base of a manipulator arm or cart. In some cases, a reference frame may be a local reference frame tied to an anatomical structure of a patient. For example, a local reference frame may be established based on the pose of an anatomical structure which the computer-assisted system may be operating on. In some cases, determinations may be made with respect to a computer-assisted system reference frame. In some cases, various reference frames may be registered to one another such that a pose in one reference frame may be understood in the context of another reference frame. Techniques and methods described herein may employ a global reference frame, local reference frame, or a combination thereof.

While some embodiments are provided herein with respect to such procedures, any reference to medical or surgical instruments and medical or surgical methods is optional and intended as non-limiting. The systems, instruments, and methods described herein may be used for animals, human cadavers, animal cadavers, portions of human or animal anatomy, non-surgical diagnosis, as well as for industrial systems and general robotic, general teleoperational, or robotic medical systems. For example, the systems and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy) and performing procedures on human or animal cadavers. Further, these techniques can also be used for surgical and nonsurgical medical treatment or diagnosis procedures.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

Referring to FIG. 1 of the drawings, a computer-assisted system for use in, for example, surgical, diagnostic, therapeutic, or biopsy procedures, is generally indicated by the reference numeral 100. As shown in FIG. 1, the medical computer-assisted system 100 generally includes a manipulator assembly 102 for operating a medical instrument 104 in performing various procedures on the patient P. The assembly 102 is mounted to or near an operating table O. An operator input system 106 allows the clinician or surgeon S to view the interventional site and to control the manipulator assembly 102.

The operator input system 106 may be located at a surgeon's console which is usually located in the same room as operating table O. However, it should be understood that the surgeon S can be located in a different room or a completely different building from the patient P. Operator input system 106 generally includes one or more control devices for controlling the manipulator assemblies 102. The control devices may include any number of a variety of input devices, such as joysticks, trackballs, data gloves, trigger-guns, hand-operated controllers, voice recognition devices, body motion or presence sensors, or the like. In some embodiments, the control devices are manual input devices which move with six degrees of freedom, and which may also include an actuatable handle for actuating instruments (for example, for closing grasping jaws, applying an electrical potential to an electrode, delivering a medicinal treatment, or the like).

FIG. 1 is a simplified diagram of a medical computer-assisted system 100 according to some embodiments. In some embodiments, medical computer-assisted system 100 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic or teleoperational systems.

As shown in FIG. 1, medical computer-assisted system 100 generally includes a manipulator assembly 102 for operating a medical instrument 104 in performing various procedures on a patient P positioned on a table T. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Operator input system 106 generally includes one or more control devices for controlling manipulator assembly 102. Manipulator assembly 102 supports medical instrument 104 and may optionally include a plurality of actuators or motors that drive inputs on medical instrument 104 in response to commands from a control system 112. The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical computer-assisted system 100 describing the rotation and orientation of the motor shafts. This position sensor data may be used to determine motion of the objects manipulated by the actuators.

Medical computer-assisted system 100 also includes a display system 110 for displaying an image or representation of the surgical site and medical instrument 104 generated by sub-systems of sensor system 108. Display system 110 and operator input system 106 may be oriented so operator O can control medical instrument 104 and operator input system 106 with the perception of telepresence.

In some embodiments, medical instrument 104 may include components of an imaging system (discussed in more detail below), which may include an imaging scope assembly or imaging instrument that records a concurrent or real-time image of a surgical site and provides the image to the operator or operator O through one or more displays of medical computer-assisted system 100, such as one or more displays of display system 110. The concurrent image may be, for example, a two or three-dimensional image captured by an imaging instrument positioned within the surgical site. In some embodiments, the imaging system includes endoscopic imaging instrument components that may be integrally or removably coupled to medical instrument 104. However, in some embodiments, a separate flexible elongated device (e.g., an endoscope), attached to a separate manipulator assembly may be used with medical instrument 104 to image the surgical site. In some examples, as described in detail below, the imaging instrument alone or in combination with other components of the medical instrument 104 may include one or more mechanisms for cleaning one or more lenses of the imaging instrument when the one or more lenses become partially and/or fully obscured by fluids and/or other materials encountered by the distal end of the imaging instrument. In some examples, the one or more cleaning mechanisms may optionally include an air and/or other gas delivery system that is usable to emit a puff of air and/or other gasses to blow the one or more lenses clean. Examples of the one or more cleaning mechanisms are discussed in more detail in International Publication No. WO/2016/025465 filed Aug. 11, 2016 disclosing "Systems and Methods for Cleaning an Endoscopic Instrument"; U.S. patent application Ser. No. 15/508,923 filed Mar. 5, 2017 disclosing "Devices, Systems, and Methods Using Mating Catheter Tips and Tools"; and U.S. patent application Ser. No. 15/503,589 filed Feb. 13, 2017 disclosing "Systems and Methods for Cleaning an Endoscopic Instrument," each of which is incorporated by reference herein in its entirety. The imaging system may be implemented as hardware, firmware, software or a combination thereof which interact with or are otherwise executed by one or more computer processors, which may include the processors of the control system 112.

Medical computer-assisted system 100 may also include control system 112. Control system 112 includes at least one memory and at least one computer processor (not shown) for effecting control between medical instrument 104, operator input system 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like.

Figures 2A, 2B:
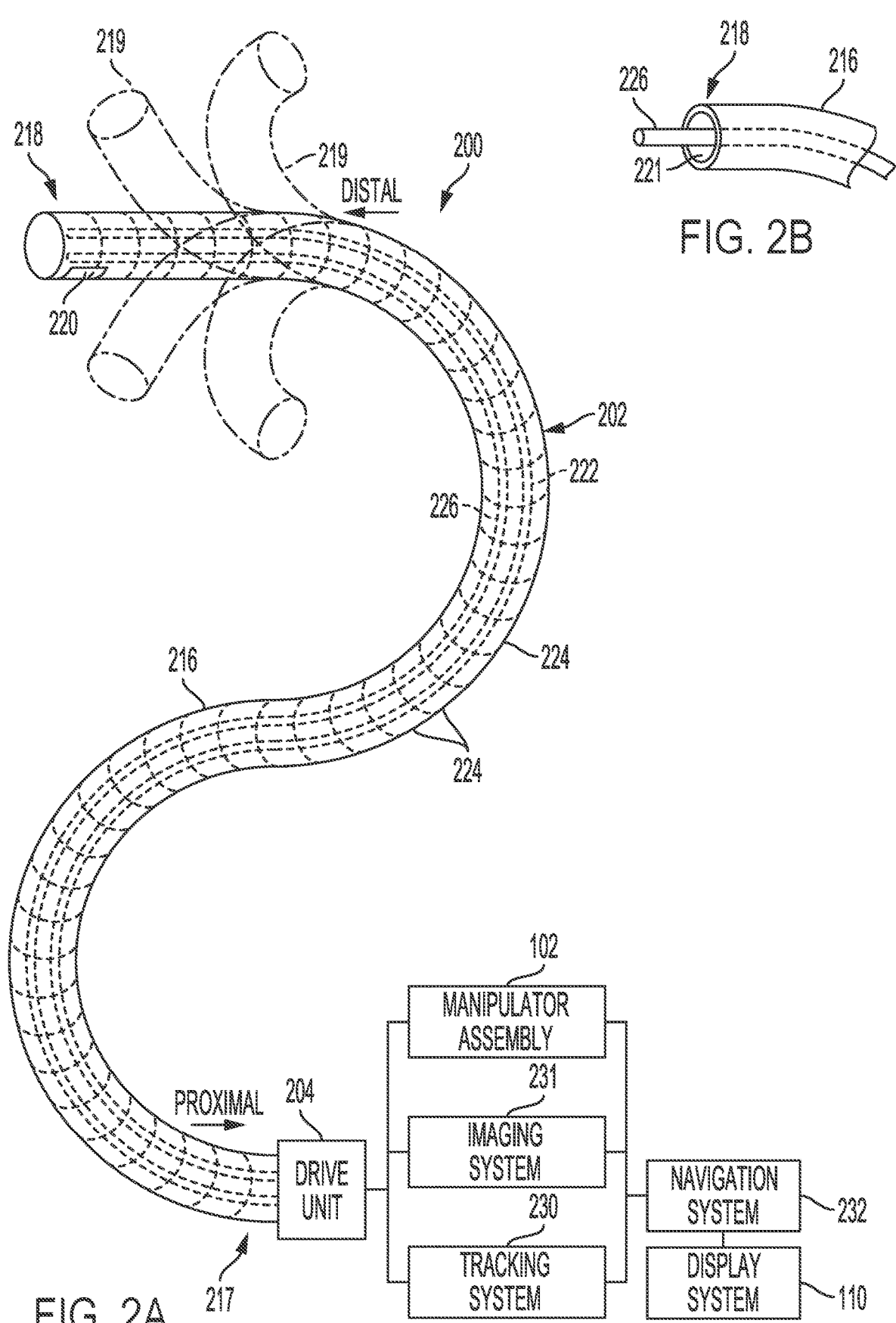
FIG. 2A illustrates a flexible elongate device, in accordance with embodiments of the present disclosure.
FIG. 2B illustrates simplified diagram of elongated flexible body, in accordance with embodiments of the present disclosure.

FIG. 2A is a simplified diagram of a medical instrument system 200 according to some embodiments. Medical instrument system 200 includes a flexible elongate device 202, such as a flexible catheter, coupled to a drive unit 204. Flexible elongate device 202 includes an elongated flexible body 216 having proximal end 217 and distal end or tip 218. Medical instrument system 200 further includes a tracking system 230 for determining the position, orientation, speed, velocity, pose, and/or shape of distal tip 218 and/or of one or more segments 224 along elongated flexible body 216 using one or more sensors and/or imaging devices as described in further detail below.

Tracking system 230 may optionally track distal tip 218 and/or one or more of the segments 224 using a shape sensor 222. Shape sensor 222 may optionally include an optical fiber aligned with elongated flexible body 216 (e.g., provided within an interior channel (not shown) or mounted externally). The optical fiber of shape sensor 222 forms a fiber optic bend sensor for determining the shape of elongated flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of elongated flexible body 216 can be used to reconstruct the shape of elongated flexible body 216 over the interval of time. In some embodiments, tracking system 230 may optionally and/or additionally track distal tip 218 using a position sensor system 220. Position sensor system 220 may be a component of an EM sensor system with position sensor system 220 including one or more conductive coils that may be subjected to an externally generated electromagnetic field. Each coil of the EM sensor system then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

Elongated flexible body 216 includes a channel 221 sized and shaped to receive a medical instrument 226. FIG. 2B is a simplified diagram of elongated flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of elongated flexible body 216 and used at a target location within the anatomy. Medical instrument 226 may include, for example, image capture probes, biopsy instruments, laser ablation fibers, and/or other surgical, diagnostic, or therapeutic tools. Medical instrument 226 may be used with an imaging instrument (e.g., an image capture probe) also within elongated flexible body 216. The imaging instrument may include a cable coupled to the camera for transmitting the captured image data. In some examples, the imaging instrument may be a fiber-optic bundle, such as a fiberscope, that couples to image processing system 231. The imaging instrument may be single or multi-spectral, for example capturing image data in one or more of the visible, infrared, and/or ultraviolet spectrums. Medical instrument 226 may be advanced from the opening of channel 221 to perform the procedure and then retracted back into the channel when the procedure is complete. Medical instrument 226 may be removed from proximal end 217 of elongated flexible body 216 or from another optional instrument port (not shown) along elongated flexible body 216.

Elongated flexible body 216 may also house cables, linkages, or other steering controls (not shown) that extend between drive unit 204 and distal tip 218 to controllably bend distal tip 218 as shown, for example, by broken dashed line depictions 219 of distal tip 218. In some examples, at least four cables are used to provide independent "up-down" steering to control a pitch of distal tip 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety.

The information from tracking system 230 may be sent to a navigation system 232 where it is combined with information from image processing system 231 and/or the preoperatively obtained models to provide the operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical computer-assisted system 100 of FIG. 1. In some embodiments, manipulator assembly 102 of FIG. 1 may be replaced by direct operator control. In some examples, the direct operator control may include various handles and operator interfaces for hand-held operation of the instrument.

According to exemplary embodiments described herein, flexible elongate device 202 may have a suitably small size and appropriate flexibility for use in small body lumens. As one example, in some embodiments an elongated flexible body 216 may have an external diameter between 3 and 4 mm. As another example, in some embodiments an elongated flexible body 216 may have an inner channel diameter no larger than 2 mm. In some applications, larger diameters may not fit into target bodily structures, such as in the more peripheral pulmonary passageways. As another example, in some embodiments a rigid portion of an elongated flexible body 216 (e.g., a distal tip 218) may have a length no larger than 5 mm. In some applications, larger lengths may eliminate flexibility required to navigate some target bodily structures. However, in some other embodiments, other dimensions both greater and less than those noted above may be employed for various structures described herein.

According to exemplary embodiments described herein, a flexible elongate device 202 may be employed to operate one or more instruments. In such an embodiment, one or more instruments may be received in a distal portion (e.g., a distal tip 218) of the flexible elongate device 202 and may be moved and/or operated with the flexible elongate device. Such instruments may include, but are not limited to, any photosensitive detector (e.g., digital camera), omnidirectional tools such as an ablation antenna or biopsy needle, and directional tools such as ultrasound probes, forceps, scalpels, and cautery instruments. It should be understood that various types of instruments may be employed with a flexible elongate device 202.

Figure 3:
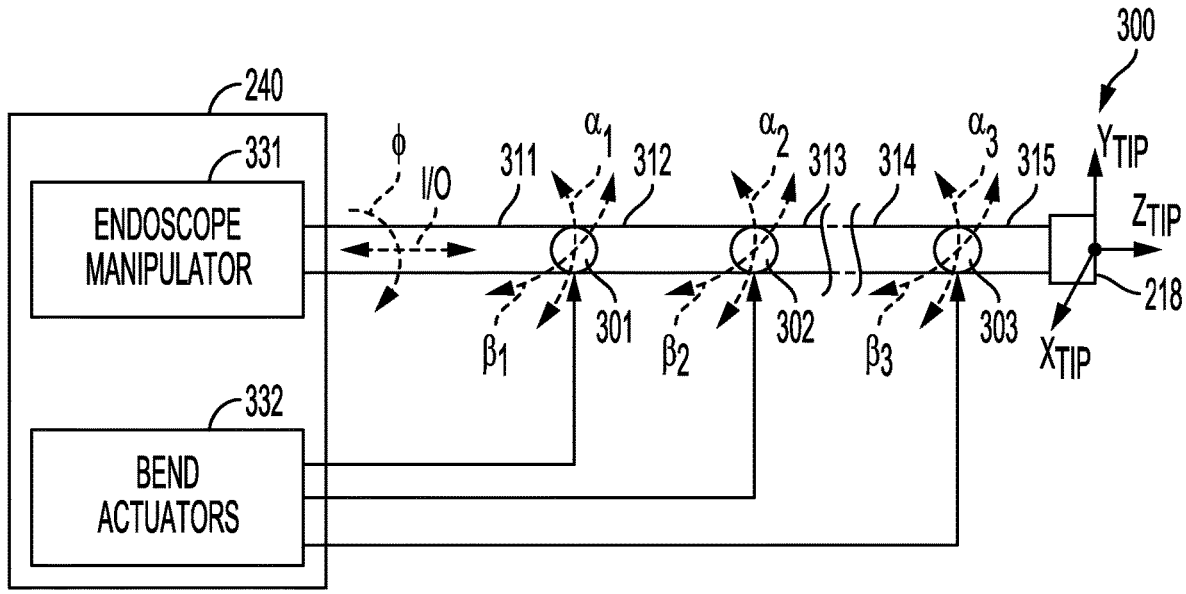
FIG. 3 illustrates an actuating system of a flexible elongate device, in accordance with embodiments of the present disclosure.

Referring to FIG. 3, an actuating system 240 for a flexible elongate device 202 may include manipulator 331 and one or more bend actuators 332. The manipulator 331 serves to actuate the flexible elongate device 202 in one or more (e.g., two) degrees of freedom. One degree of freedom is an insertion/retraction movement (as illustrated by the dotted line, two-headed arrow labeled "I/O") implemented with a prismatic joint that moves the proximal end 217 of the computer-assisted flexible elongate device 202 forward and backward, with forward motion corresponding with insertion of the flexible elongate device 202 within an anatomy and backward motion corresponding with retraction of the flexible elongate device 202 from the anatomy. The other degree of freedom is a proximal roll rotation (as illustrated by the dotted line, two-headed arrow labeled "γ") implemented with a rotary joint that rotates the flexible elongate device 202 about its insertion/retraction direction. In other embodiments, only one degree of freedom may be provided (e.g., insertion/retraction) and no roll rotation degree of freedom may be provided. The bend actuators 332 actuate one or more bending segments 301, 302, 303. For example, the bend actuator 332 actuates bending segments 301, 302, 303 of the flexible elongate device 202 so they are each articulable in respective pitch rotations (as illustrated by the dotted line, two-headed arcs $\alpha_1$-$\alpha_3$) and yaw rotations (as illustrated by the dotted line, two-headed arcs ($\beta_1$-$\beta_3$). In addition to the articulable segments, a first link 311 of the elongate device 202 is coupled at its proximal end, either directly or with an intervening elongated flexible body 216, to the manipulator 331 and at its distal end to rest of the elongated flexible body 216 so that as the manipulator 331 causes the link 311 to move in either the I/O direction or roll rotation ($\varphi$), then the rest of the elongated flexible body 216 (and in particular, all of the articulable segments 301-303 and coupling links 312, 313, 314, 315 that couple with the articulable segments 301, 302, 303) move in unison with the first link 311. In some other embodiments, only a distal portion of the flexible elongate device 202 may articulate. In some such embodiments, the flexible elongate device 202 may include four steer wires (e.g., two for pitch and two for yaw). The steer wires may be connected to corresponding actuators at a proximal end of each pull wire and to the distal portion of the flexible elongate device 202 at the distal end of each pull wire. The more proximal portions of the flexible elongate device 202 may not be articulable, in some embodiments. In such embodiments, the elongated flexible body 216 of the flexible elongate device 202 may be configured conform to a passageway structure and the steer wires may not directly apply force to the elongated flexible body 216.

A stereoscopic or monoscopic imaging device (also referred to as a "camera") may be removably disposed at the distal tip 218 of the flexible elongate device 202 for capturing images that are transmitted to and processed by the imaging system 231 and displayed on the display system 110. In some embodiments, one or more of fiber optic cables (e.g., shape sensor 222) may be coupled at their proximal end to a light source (not shown) for illumination purposes at the distal tip 218. A distal tip reference frame 300 is defined at the distal tip 218 by a depth axis $Z_{TIP}$, a horizontal axis $X_{TIP}$ and a vertical axis)(Tip of a view of the camera as it looks away from the distal tip 218. As discussed above, the presence of the camera within the distal tip 218 and the relative rotational orientation of the camera with respect to the distal tip reference frame 300 may be important for computer-assisted control of the system. Additionally, the longitudinal position of the camera within the distal tip 218 may be important for computer-assisted control of the system. As the camera is removably disposed in the distal tip 218, the relative rotational orientation and longitudinal position may change as the camera is removed or added to the flexible elongate device 202. In some embodiments, a computer-assisted system may be configured to provide a display of an image captured by the camera at the distal tip 218 (e.g., at display system 110). In some embodiments, the computer-assisted system may be configured to rotate the image displayed based on a determined relative rotational orientation of the camera, as discussed further herein. For example, the image displayed may be rotated such that an upward direction on the display corresponds to a vertical direction of the distal tip 218 in the distal tip reference frame 300 (e.g., $Y_{TIP}$). In this manner, the image from a camera may be registered to the directionality of the display system 110 (e.g., by imaging processing system 231) by rotating the image provided by the camera based on the determined relative rotational orientation.

In some embodiments, a camera may be removed from a distal tip 218 of a flexible elongate device 202 and replaced with another type of instrument. In some such embodiments, the presence, longitudinal position, and rotational orientation of any instrument with respect to the distal tip reference frame 300 may be important for computer-assisted control of the instrument. As discussed further below with reference to exemplary embodiments, a flexible elongate device may employ magnetic field generators and magnetic field sensors to determine an axial alignment of an instrument within a channel of an elongated flexible body 216 (e.g., along a longitudinal axis of the elongated flexible body 216), and/or determine the relative rotational orientation about the longitudinal axis. In some embodiments, a camera may be integrated with the flexible elongate device 202. In some such embodiments, the relative orientation of the camera to the distal tip reference frame 300 may be constant, and techniques described herein regarding rotational orientation detection may be employed for another type of instrument which may be removable from the flexible elongate device 202.

Figure 4:
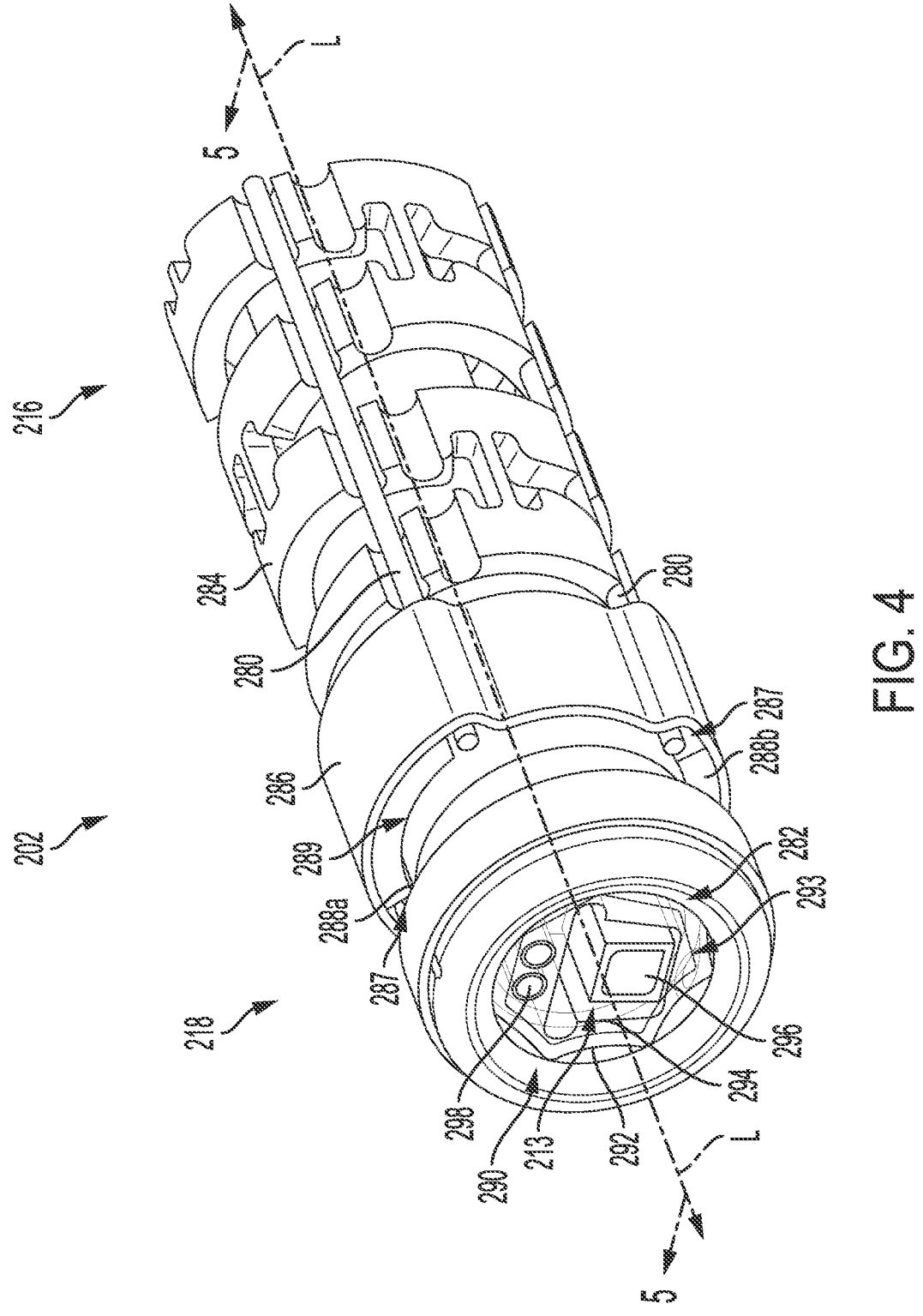
FIG. 4 illustrates a distal portion of a flexible elongate device, in accordance with embodiments of the present disclosure.

FIG. 4 illustrates a distal portion of a flexible computer-assisted system, in accordance with embodiments of the present disclosure. The flexible computer-assisted system includes a flexible elongate device 202 and an instrument 213. The arrangement depicted in FIG. 4 may be employed with the computer-assisted systems of FIGS. 1-3, in some embodiments. As shown in FIG. 4, the distal portion of the flexible elongate device 202 includes an elongated flexible body 216 with a steerable distal tip 218. The elongated flexible body 216 includes a flexible support structure 284 that allows the elongated flexible body 216 to bend. The flexible support structure 284 may correspond to a flexible tube including patterned slots formed therein, a flexible tube formed from a flexible material, interconnected segments that are configured to pivot relative to one another, and/or any other appropriate flexible structure. The elongated flexible body 216 includes an internal channel 282 that extends along a longitudinal axis L of the elongated flexible body 216. Wires 280 are employed with the embodiment of FIG. 4 to steer the distal tip 218. In particular, applying tension to the wires 280 may bend the support structure 284, thereby steering the distal tip 218 in a desired direction. In some embodiments, control of the wires 280 may be automated or semi-automated by a computer-assisted system. The distal tip 218 may be rigid such that application of force by the wires 280 does not substantially bend the distal tip 218 but does bend the elongated flexible body 216.

As shown in FIG. 4, the distal tip 218 may be sized and shaped to accommodate the instrument 213. The instrument 213 of FIG. 4 includes a photosensitive detector 296, which may be configured as a digital camera, in some embodiments, though other appropriate instruments may also be used as noted above. The photosensitive detector 296 is oriented in a distal direction out of the instrument 213. The photosensitive detector 296 may be configured to provide information to an operator of the flexible computer assisted system (e.g., via a display system 110) regarding the operating environment of the distal tip 218. In some embodiments as shown in FIG. 4, the instrument 213 includes a light source 298, which may be employed for illumination. In some embodiments, the light source 298 may be an optical fiber, a light emitting diode (LED) or some other illumination source. The rotational orientation of the photosensitive detector 296 about the longitudinal axis L may be important to register images captured by the photosensitive detector 296 to one or more reference frames used by the flexible computer-assisted system. For example, it may be desirable to align the reference frame of the distal tip 218 of the flexible elongate device 202 to images captured by the photosensitive detector 296. The alignment allows the image output by the photosensitive detector 296 to be displayed in a manner that intuitively reflects a corresponding change in the articulated direction of the distal tip 218. In terms of a local reference frame of an operator, for example, it may be desirable that an image reflects a rightward movement when the distal tip 218 is steered rightward, and similarly for other directions. Accordingly, as discussed above, it is desirable to be able to track the rotational orientation of the photosensitive detector 296 and other portions of the instrument 213 with reference to the rotational orientation of the flexible elongate device 202.

According to the embodiment of FIG. 4, the distal tip 218, or other portion of the elongated flexible body 216 of the flexible elongate device 202, may include a magnetic field generator 289. In the embodiment of FIG. 4, the magnetic field generator 289 includes a first magnet 288a and a second magnet 288b. The first and second magnets 288a, 288b may be permanent magnets that are arranged such that anti-poles (e.g., north and south poles) face one another from opposing sides of the channel 282 of the elongated flexible body 216. For example, a north pole of each of the first and second magnets 288a, 288b face the same direction. Correspondingly, a south pole of the first magnet 288a may face a north pole of the second magnet 288b. Such an arrangement produces magnetic field lines through the channel 282 that are substantially unidirectional and uniform and having a direction from one of the magnets to the other one of the magnets. As discussed further below, such an arrangement may allow the rotational orientation of the first magnet 288a and the second magnet 288b about an axis (e.g., a longitudinal axis of channel 282) to be determined via a magnetic field sensor (e.g., see magnetic field sensor 324 in FIG. 5) disposed within the channel 282. In particular, the direction of the magnetic field lines detected by the magnetic field sensor will change depending on the rotational orientation of the magnetic field generator 289 relative to instrument 213. In some embodiments as shown in FIG. 4, the magnetic field generator 289 may be rotationally fixed to the elongated flexible body 216. One example of such a magnetic arrangement will be discussed further with reference to FIG. 10. The first and second magnets 288a, 288b may be disposed within a shield 286. The shield 286 may be ferromagnetic and configured to complete a magnetic circuit between the first and second magnets 288a, 288b. Additionally, the shield 286 may be employed to shape the direction of magnetic field lines, such that the magnetic field direction through the channel 282 is substantially unidirectional. The shield 286 may also be employed to inhibit a magnetic field from extending substantially outside of the distal tip 218, where the field could interference with other electronics (e.g., pacemakers) disposed outside of a computer-assisted system or other components of the computer-assisted system. The shield 286 may also increase magnetic field strength inside of the channel 282. Increased field strength is not only beneficial from the perspective of a signal-to-noise ratio. If another device produces a competing magnetic field, the shield 286 will also help to isolate a magnetic field sensor from this noise. The presence, position, and orientation of the magnetic field generated by the magnetic field generator 289 of FIG. 4 may be determined by a processor using information from the magnetic field sensor (e.g., a Hall effect sensor), as discussed below with reference to FIG. 5. While in the embodiment of FIG. 4 permanent magnets are employed, in other embodiments, electromagnets or other suitable types of magnetic structures may be employed.

According to the embodiment of FIG. 4, a magnetic field generator 289 (e.g., first magnet 288a and second magnet 288b) is disposed radially outwards from, and may at least partially surround, the instrument 213 when it is disposed in the channel 282 of the elongated flexible body 216. The magnetic field generator 289 may be attached to the elongated flexible body 216 in some embodiments. A magnetic field sensor, configured to detect a presence, position, and orientation of the magnetic field generated by the magnetic field generator, may be attached to the instrument 213, an example of which will be shown in FIG. 5. In other embodiments, a magnetic field generator 289 may be attached to an instrument 213, and one or more magnetic field sensors may be attached to an elongated flexible body 216. In such an arrangement, the magnetic field sensor may be disposed radially outward relative to the instrument 213 with respect to the longitudinal axis L if the elongated flexible body 216 when the instrument 213 is disposed in the elongated flexible body 216.

In some embodiments, the instrument 213 may mate with the flexible elongate device 202 (e.g., at distal tip 218) in one of a limited number of discrete orientations. The instrument 213 may include an instrument housing 293 that includes a plurality of mating flats 294. The mating flats 294 may be a first set of angled flats disposed around an outer cross-sectional perimeter of the mating instrument portion. As shown in FIG. 4, the distal tip 218 may include a tip cap 290 that includes a plurality of orienting flats 292. The elongated flexible body 216 of the flexible elongate device 202 may include a mating channel portion disposed along a length of the channel 282 extending through the elongated flexible body 216. The mating channel portion may include the orienting flats 292 as a second set of angled flats disposed around an inner cross-sectional perimeter of the mating channel portion. The mating channel portion may be arranged along a length of the channel 282 of the elongated flexible body 216 such that it mates with the mating instrument portion of the instrument 213 when the instrument is inserted into the channel 282 of the elongated flexible body 216. In some embodiments, the corresponding angled flats may allow for interlocking of the instrument 213 and the elongated flexible body 216 in a finite number of rotational orientations (e.g., at least two). The number of angled flats provided on each of the mating portions may determine the number of possible locked rotational orientations of the instrument 213 relative to the elongated flexible body 216.

As discussed above, when the instrument 213 is distally inserted within the channel of 282 elongated flexible body 216 to the distal tip 218, the mating flats 294 mate with the orienting flats 292 in the discrete number of possible orientations. In some embodiments, the orienting flats 292 and mating flats 294 may have corresponding shapes to facilitate effective mating of the orienting flats 292 and mating flats 294. In some embodiments as shown in FIG. 4, the orienting flats 292 and mating flats 294 may be flats. As used herein, a "flat" may be a planar surface. In other embodiments, corresponding orienting surfaces and mating surfaces may be curved or have any other appropriate shape, including non-flat shapes. The housing of the instrument 213 and the distal tip 218 may include a corresponding number of orienting flats 292 and mating flats 294. The number of mating flats 294 may determine the number of discrete rotational orientations of the instrument 213 with respect to the elongated flexible body 216 when the instrument 213 is placed into the channel 282. For example, if seven orienting flats 292 are employed, as shown in FIG. 4, the instrument 213 may be able to be inserted into the distal tip 218 in one of seven rotational orientations about the longitudinal axis L. An arrangement of an instrument 213 and distal tip 218 with mating flats 294 and orienting flats 292 may increase the accuracy and decrease computational difficulty of a rotational orientation determination based on magnetic field information (e.g., generated by first magnet 288a and second magnet 288b). In particular, rather than all rotational orientation angles being possible for mating, such an arrangement reduces the possible rotational orientation angles to a limited number of discrete possibilities, thereby increasing accuracy and confidence in orientation determination. For example, each orienting flat 292 may be associated with a range of measured rotational angles about the longitudinal axis L. Accordingly, a magnetic field sensor may be employed to determine a measured rotational angle, which is then fit to one of the possible discrete rotational orientations of the instrument 213 with respect to the distal tip 218. As such, errors or inaccuracies caused by the use of magnetic field information to determine the rotational orientation may be reduced or eliminated, and a reliable rotational orientation of the instrument 213 may be determined based on the magnetic field information. Accordingly, in some embodiments, a discrete orientation determined based on the alignment of orienting flats 292 and mating flats 294 may not be used alone for a determination of rotational orientation but may rather be used as a supplement to reduce error associated with an absolute position determined based on magnetic field sensing.

Embodiments herein may employ any number of mating flats 294 and orienting flats 292 associated with the elongated flexible body 216 and the instrument 213. The number of corresponding mating flats 294 and orienting flats 292 provides a tradeoff between ease of use and accuracy. More flats may result in lesser accuracy as the range of angles associated with each flat is smaller and determining alignment with that particular angle range may be more difficult, but the instrument 213 may be easier to seat in a specific orientation for a user. Accordingly, additional flats may reduce the accuracy of angular determination based on the alignment with a mating flat. For example, narrowing possible rotational orientations to twelve different orientations (e.g., where there are twelve corresponding mating flats 294 and orienting flats 292) may result in a less accurate position determination than narrowing possible rotational orientations to two different orientations (e.g., where there are two corresponding mating flats 294 and orienting flats 292). Correspondingly, fewer flats may result in greater accuracy for a final absolute position determination as the range of angles associated with each flat is larger, but the instrument 213 may be more difficult to seat in a desired orientation for a user. A single mating flat would have total accuracy, as there would only be one possible orientation for the instrument 213 within the flexibly body 216. In some embodiments, between 4 and 12 mating flats 294 and orienting flats 292 may be employed on an instrument 213 and corresponding portion of an elongated flexible body 216 (e.g., the distal tip 218). Examples of such embodiments are shown and described with reference to FIGS. 11-16.

Figure 5:
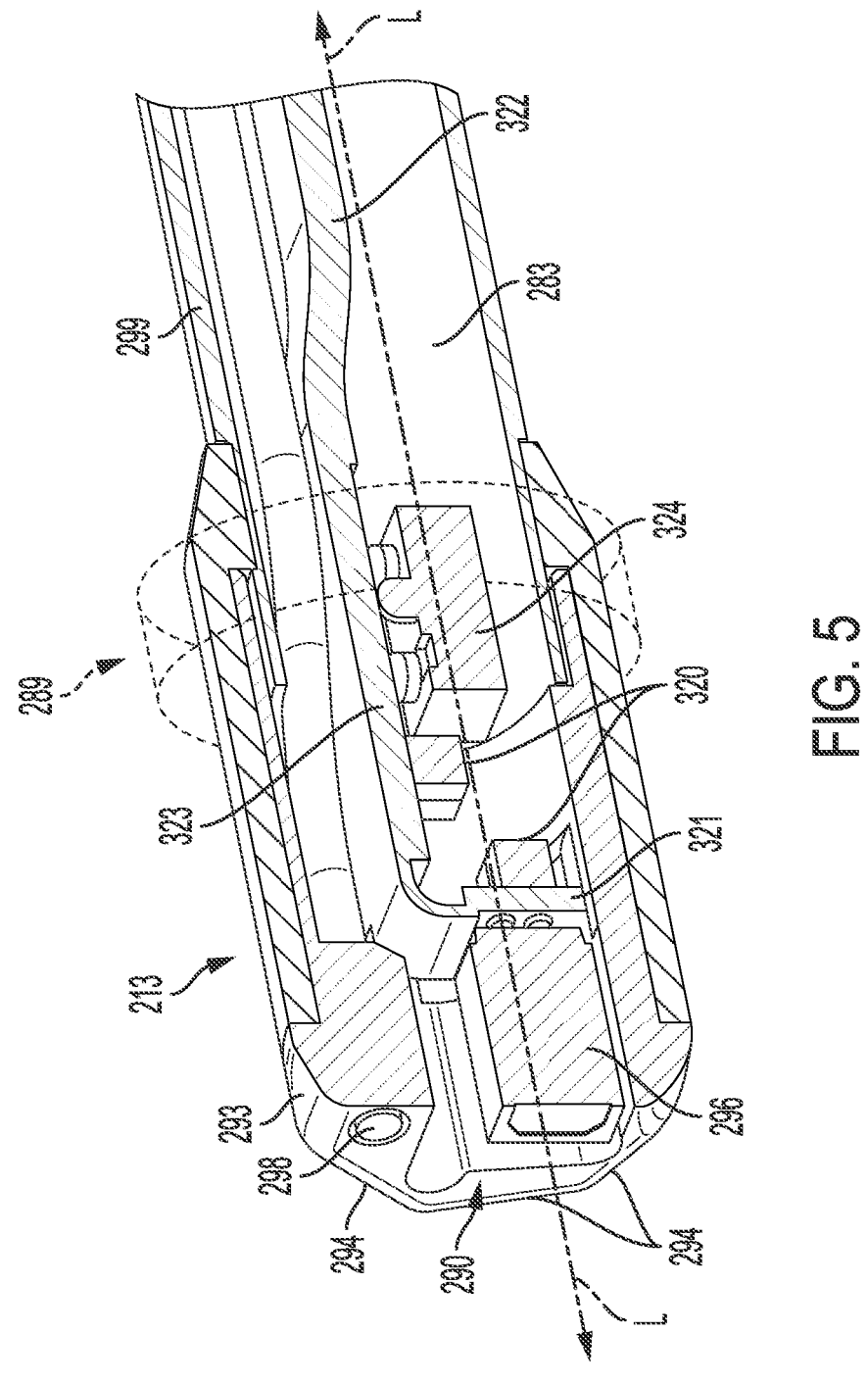
FIG. 5 illustrates a cross-section of the distal portion of FIG. 4 taken along line 5-5.

FIG. 5 illustrates a cross-section of the distal portion of the instrument 213 of FIG. 4 facing in the direction of line 5-5. In this example, the instrument 213 is an imaging probe configured to generate image data. The instrument 213 includes an instrument housing 293. The instrument housing 293 may house the various components of the instrument 213 at a distal portion of the instrument 213. The instrument housing 293 may be substantially rigid in some embodiments. When inserted within the channel 282 of the flexible elongate device 202, the instrument housing 293 may extend to the distal tip 218 of the elongated flexible body 216 of the flexible elongate device 202. In the embodiment of FIG. 5, the instrument housing 293 includes a plurality of mating flats 294. The plurality of mating flats 294 of the instrument 213 may be configured to engage the plurality of orienting flats 292 of the elongated flexible body 216 (e.g., as shown in FIG. 4) to restrict the relative rotational orientation between the elongated flexible body 216 and the instrument 213 to a plurality of discrete orientations when the instrument 213 is inserted into the elongated flexible body 216. As shown in FIG. 5, the instrument housing 293 may be coupled to a flexible sheath 299. The flexible sheath 299 may contain power and data connections (e.g., wire housing 322) used by devices within the instrument housing 293. The flexible sheath 299 and instrument housing 293 may extend through the channel 282 of the elongated flexible body 216 (e.g., as shown in FIG. 4), which extends along a longitudinal axis L.

As shown in FIG. 5, the photosensitive detector 296 is disposed in an interior channel 283 of the instrument housing 293. The photosensitive detector 296 includes a circuit board 321. The photosensitive detector 296 has a data and power connection via wiring that may be contained within a wire housing 322. The wire housing 322 may house one or more wires including power and/or data wires for connecting the photosensitive detector 296 and the magnetic field sensor 324. In other embodiments, the photosensitive detector 296 may be a RGB camera, infrared (IR) camera, stereoscopic camera, depth camera, fiber optic camera, wireless camera, or any other photosensitive detector with wired or wireless connections. In some embodiments, decoupling capacitors 320 may be operatively coupled with the photosensitive detector 296 to compensate for the effect of inductance over long cable runs. Such an arrangement may assist in providing instantaneous current to the photosensitive detector 296 and other powered components. As shown in FIG. 5, the instrument 213 may further include a light source 298, such as a fiber optic cable (e.g., that carries light from a more proximal light generator) or an LED. When the light source 298 is an LED or other light generator, the light source 298 may be powered via a wire that runs through the flexible sheath 299.

The instrument 213 of FIG. 5 may also include a magnetic field sensor 324. The magnetic field sensor 324 may be a Hall effect sensor (e.g., Lorentz force device) in some embodiments. In other embodiments, a magnetoresistive sensors, flux-gate magnetometer, or a magnetoinductive sensor may be employed as the magnetic field sensor 324. The magnetic field sensor 324 may be configured to detect a presence, position, and orientation of a magnetic field. In some embodiments, the magnetic field sensor 324 may be configured to detect an orientation of a magnetic field in three-dimensional space (e.g., determine a three-dimensional vector). For example, the magnetic field sensor 324 may be a three-dimensional integrated Hall effect sensor. In other embodiments, the magnetic field sensor 324 may be configured to detect an orientation of a magnetic field in a two-dimensional space (e.g., determine a planar vector). For example, the magnetic field sensor 324 may be configured to detect magnetic field direction along at least two perpendicular axes so that the rotational orientation of the magnetic field sensor 324 with respect to one or more magnetic field generators may be determined about a single axis (e.g., the longitudinal axis L). The magnetic field sensor 324 may be configured to measure magnetic field strength along the two perpendicular axes so that different field strengths about the axes may be associated with different rotational orientations of the instrument 213. The magnetic field sensor 324 may be disposed in a portion of the channel 282 of the flexible elongate device to intersect a plane formed by the magnetic field lines from the magnetic field generator 289 over a 360-degree rotation of the instrument 213. In such an arrangement the direction of the magnetic field lines detected by the magnetic field sensor 324 may be used to determine a rotational orientation of the instrument 213 relative to an elongated flexible body 216 that includes the magnetic field generator. In some embodiments as shown in FIG. 5, the magnetic field sensor 324 may be disposed approximately at a radial center of the interior channel 283. Such a position may be equidistance from the different magnets of the magnetic field generator 289 disposed on the elongated flexible body 216 regardless of the orientation of the instrument 213 about the longitudinal axis L. In some embodiments, the magnetic field sensor 324 is disposed on the longitudinal axis L of the elongated flexible body 216. However, in other embodiments, the magnetic field sensor 324 may be disposed in a position spaced from the longitudinal axis L. In some embodiments, a sensing portion of the magnetic field sensor 324 may be spaced from the radial center of the interior channel 283 (e.g., the sensing portion may be off-center relative to the longitudinal axis L).

In some embodiments, the magnetic field sensor 324 includes a circuit board 323. The circuit board 323 of the magnetic field sensor 324 and the circuit board 321 of the photosensitive detector 296 both connect to the wire housing 322. In some other embodiments, no wire housing may be employed to house one or more wires. In the embodiment of FIG. 5, the magnetic field sensor 324 shares power but not data connections with other components of the instrument 213 (e.g., the photosensitive detector 296). Separate power and/or data wires for both photosensitive detector 296 and the magnetic field sensor 324 may be housed in the wire housing 322. The magnetic field sensor 324 may share any combination of power and/or data connections with the photosensitive detector 296 in other embodiments. In some embodiments, information from the magnetic field sensor 324 may be provided to at least one processor, which may use the information to determine direction of the magnetic field encountered by the magnetic field sensor 324, the presence of the instrument 213 within the elongated flexible body 216 (e.g., based on detection of the magnetic field by the magnetic field sensor 324), a longitudinal position of the instrument 213 within the elongated flexible body 216 (e.g., based on detection of the position of the magnetic field by the magnetic field sensor 324), and a rotational orientation of the instrument 213 about the longitudinal axis L with respect to the elongated flexible body 216. In some embodiments, some or all of this processing may be performed by processing circuitry integrated with the magnetic field sensor 324.

The instrument 213 may be various types of instruments, such as an imaging probe, a biopsy needle, an ablation probe, an electroporation probe, etc. In the example of FIG. 5, the instrument 213 is an imaging probe that includes the photosensitive detector 296 and the light source 298. These imaging components may be excluded from the instrument 213 when the instrument is not an imaging probe. In some embodiments, these imaging components may be integrated with the flexible elongate device 202 to provide simultaneous imaging and other functionality provided by a different type of instrument. For any type of instrument, magnetic field sensors and generators may be used to provide for one or more of presence detection, longitudinal position determination, and rotational orientation determination as discussed herein.

Figure 6:
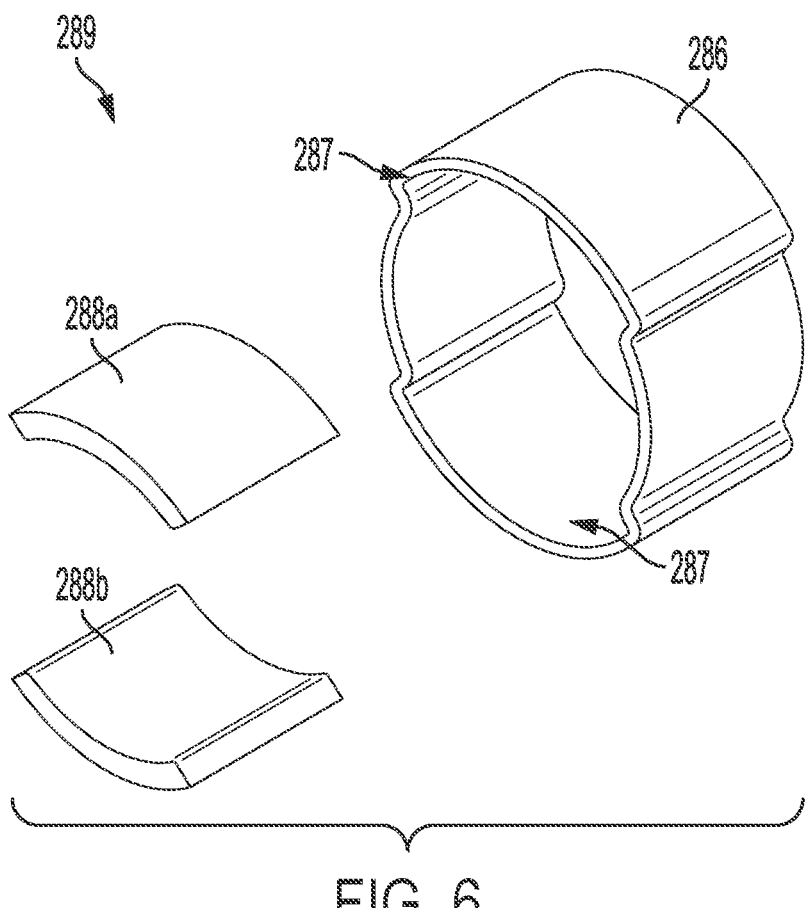
FIG. 6 illustrates an exploded view of a magnetic field generator, in accordance with embodiments of the present disclosure.
Figure 7:
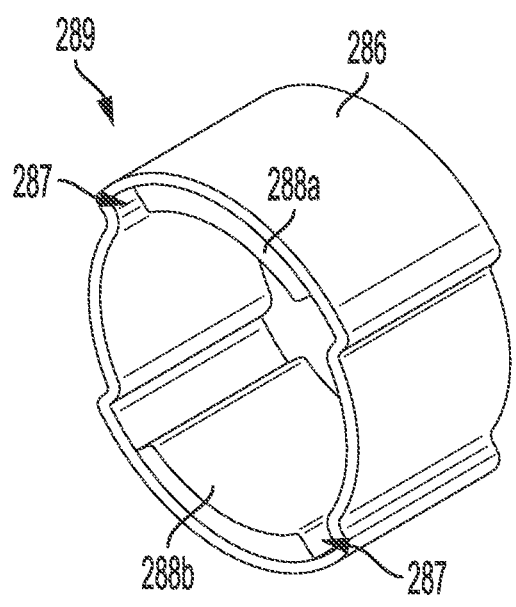
FIG. 7 illustrates an assembled view of the magnetic field generator of FIG. 6.

FIG. 6 illustrates an exploded view of a magnetic field generator 289, in accordance with embodiments of the present disclosure. FIG. 7 illustrates an assembled view of the magnetic field generator 289 of FIG. 6. The magnetic field generator 289 includes the magnets 288a and 288b and may include a shield 286, in some embodiments. The shield 286 may be formed of a ferromagnetic material, such that it is able to complete a magnetic circuit to strengthen, shape and contain the magnetic field lines. In some embodiments, the shield 286 may be composed of magnetic stainless-steel, nickel-iron alloy, regular steel, soft iron, cobalt-iron alloy, or any other magnetic material. The shield 286 may aid in shaping the generated magnetic field lines to be substantially unidirectional through a channel 282 of an elongated flexible body 216 of the flexible elongate device 202 where the instrument's sensor 324 would sit when instrument 213 may be inserted. The unidirectionality of the magnetic field lines may be employed such that the directionality of the magnetic field may be more reliably determined over a full 360-degree rotation of the instrument 213 disposed in the channel 282. The magnetic field generator 289 may include one or more magnets. In the embodiment of FIGS. 6 and 7, the magnetic field generator 289 includes two permanent arc-shaped magnets. A first magnet 288a and a second magnet 288b are disposed on opposing sides of the channel 282 of the elongated flexible body 216. The magnets 288a, 288b are each secured inside a receptacle 287 of the shield 286. In some embodiments, the magnets 288a, 288b may be secured with an adhesive, screws, or other suitable fastener. The magnets 288a, 288b may be arranged such that antipoles face one another. Such an arrangement may encourage the formation of unidirectional magnetic field lines through at least the portion of channel 282 where sensor 324 may reside when instrument 213 may be inserted, as discussed further with reference to FIGS. 8-10. In some embodiments, the shield 286 may be press fit to the elongated flexible body 216. In some embodiments, the shield 286 may be attached to the elongated flexible body 216 using an adhesive, screws, or another suitable fastener.

While two partial cylindrical arc-shaped magnets 288a, 288b are used in the embodiments of FIGS. 4, 6 and 7, in other embodiments a magnetic field generator 289 may have any suitable arrangement depending on the particular packaging desired. In some embodiments, a magnetic field generator 289 may be annular (e.g., a cylindrical ring). In some embodiments, a magnetic field generator 289 may be flat. Accordingly, it should be understood that any type (e.g., different numbers of magnets) and/or shape of magnetic field generator 289 may be employed with the systems disclosed herein to create a magnetic field that is different for different rotational orientations of a magnetic field sensor.

In some embodiments, a magnetic field generator is disposed on an instrument and the magnetic field sensor is on a flexible elongate device. For example, one or more magnetic field sensors, able to sense the magnetic field in two or more perpendicular dimensions, may be attached to an elongated flexible body of the flexible elongate device, and a magnetic field generator may be attached to the instrument. In such an arrangement, one or more magnets of the magnetic field generator may be arranged in (e.g., a center portion of) an instrument, and in some cases may be aligned on a longitudinal axis of the instrument about which the rotational orientation of the instrument may be determined. With the magnet field generator secured to the instrument, the magnetic field generator may function as a detectable reference frame of the instrument that may be registered to a reference frame of a distal tip of a flexible elongate device. For example, the direction of magnetic field lines generated by the magnetic field generator may be representative of a reference frame of the instrument and may be detectable by one or more magnetic field sensors. The elongated flexible body may include one or more magnetic field sensors disposed about a longitudinal axis of the elongated flexible body radially outward from the instrument. Two or more magnetic field sensors may be used and may be separated and arranged at approximately 90 degrees from each other about the longitudinal axis. Such an arrangement may promote the sensed magnetic field lines from the magnetic field generator to be different for different rotational orientations of the instrument. A shield may be disposed in the flexible body, surrounding the one or more magnetic field sensors.

Figure 8:
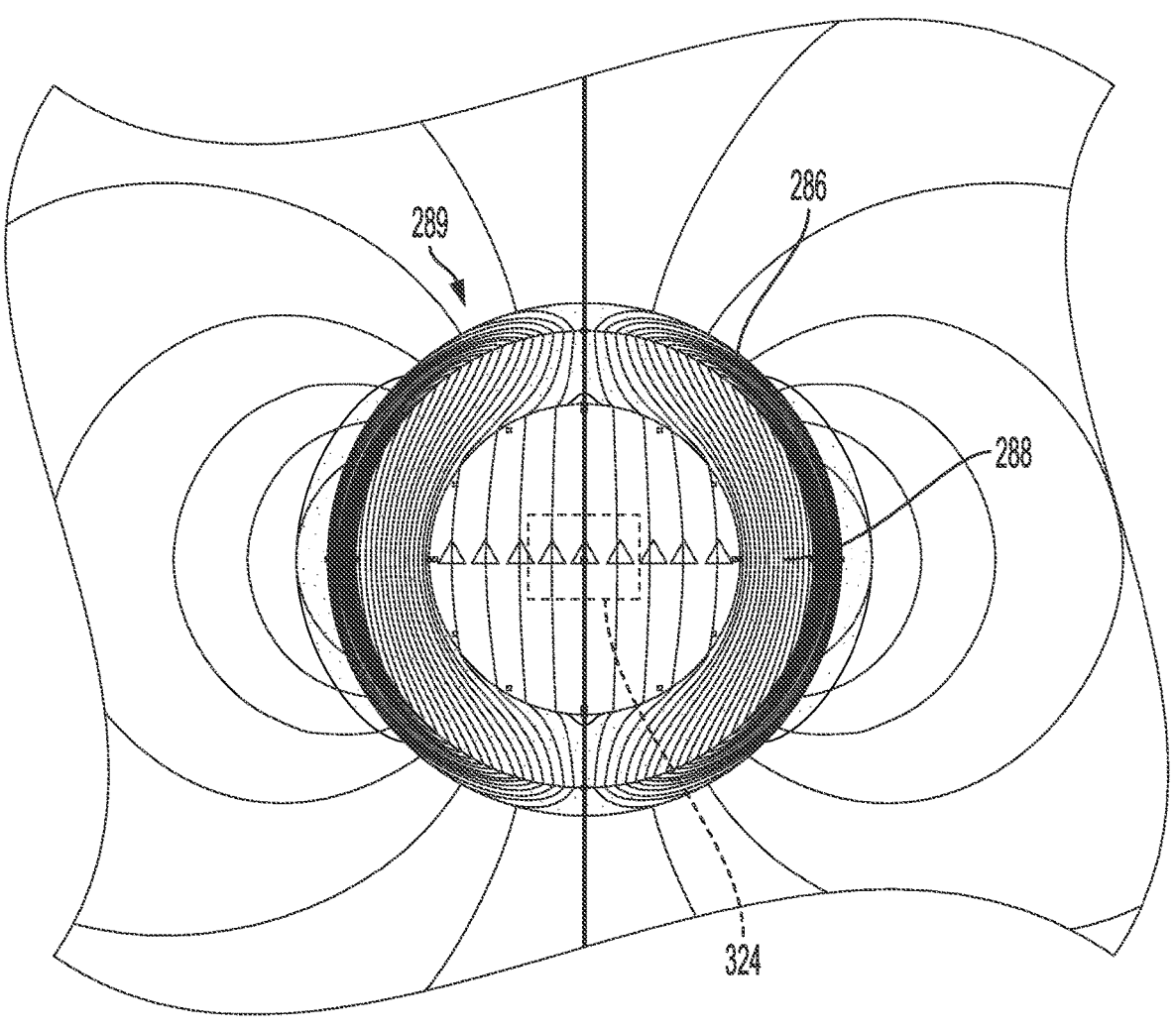
FIG. 8 illustrates a magnetic field generated by a magnetic field generator in accordance with one embodiment.

FIG. 8 illustrates a magnetic field generated by a magnetic field generator 289 in accordance with one embodiment. In the embodiment of FIG. 8, the magnetic field generator 289 includes a shield 286 and an annular permanent magnet 288. The annular magnet 288 is arranged such that the magnetic field direction inside of the annular magnet 288 is substantially unidirectional. That is, the magnetic field generated by the magnet 288 within a center of the magnet is substantially uniform (e.g., of similar strength) and unidirectional. Accordingly, the direction of the magnetic field may act as a detectable reference frame for determination of a rotational orientation of an instrument. As shown in FIG. 8, a magnetic field sensor 324 disposed on an instrument located within this magnetic field may be used to determine a presence, position, and orientation of the magnetic field. As the magnetic field within the channel may be unidirectional, any relative rotation of the instrument when seated may be determined reliably. In some embodiments, the magnetic field sensor 324 may be positioned as close to the center of the annular magnet as possible to ensure the magnetic field lines are as uniform as possible. In some embodiments, the center of the magnetic field generator 289 may be an axis of rotation of an instrument for seating within an elongated flexible body, which may also be collinear with a longitudinal axis of the instrument and/or elongated flexible body. However, instances in which the instrument and associated detector are offset from either of these axes are also contemplated.

Figure 9:
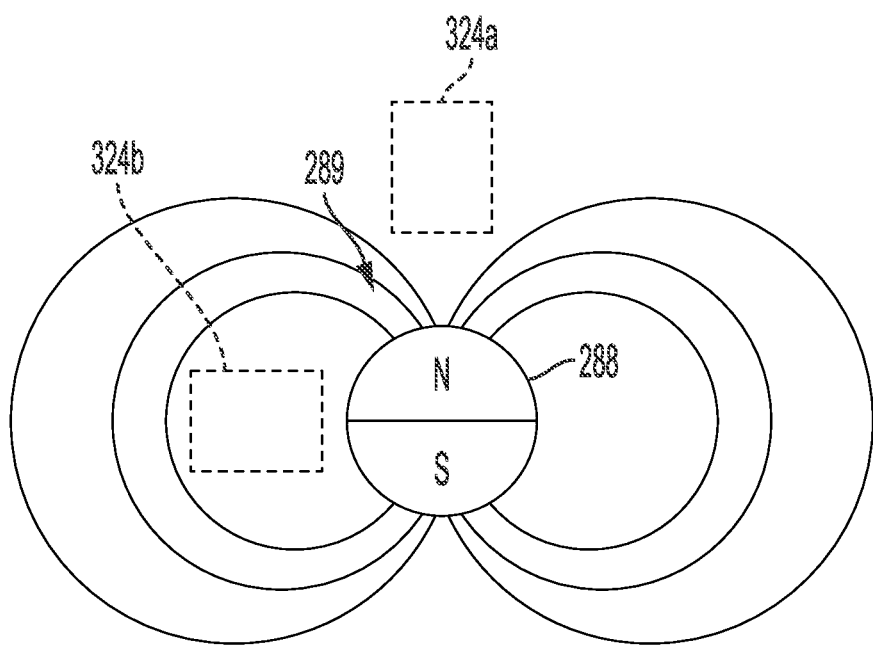
FIG. 9 illustrates a magnetic field generated by a magnetic field generator in accordance with another embodiment.

FIG. 9 illustrates a magnetic field generated by a magnetic field generator 289 in accordance with another embodiment. As shown in FIG. 9, the magnetic field generator 289 includes a cylindrical magnet 288. A first magnetic field sensor 324a and a second magnetic field sensor 324b are configured to detect the presence, position, and orientation of the magnetic field generated by the magnetic field generator 289. The direction of the magnetic field lines may be employed to determine an orientation of the magnetic field, which in turn may be employed to determine an orientation of the magnetic field generator 289. In some embodiments as discussed above, a magnetic field generator 289 may be employed in an instrument and one or more magnetic field sensors, able to sense the magnetic field in two or more perpendicular dimensions, may be employed in an elongated flexible body to determine an orientation of an instrument based on the magnetic field emitted from the instrument. The magnetic field generator 289 of FIG. 9 may be employed in some such embodiments. It may be desirable to position two or more magnetic field sensors 324a, 324b at an approximately 90-degree offset from one another as shown in FIG. 9. Such an arrangement may better capture the magnetic field lines to determine a direction of all rotational orientations of an instrument including the magnetic field generator 289.

Figure 10:
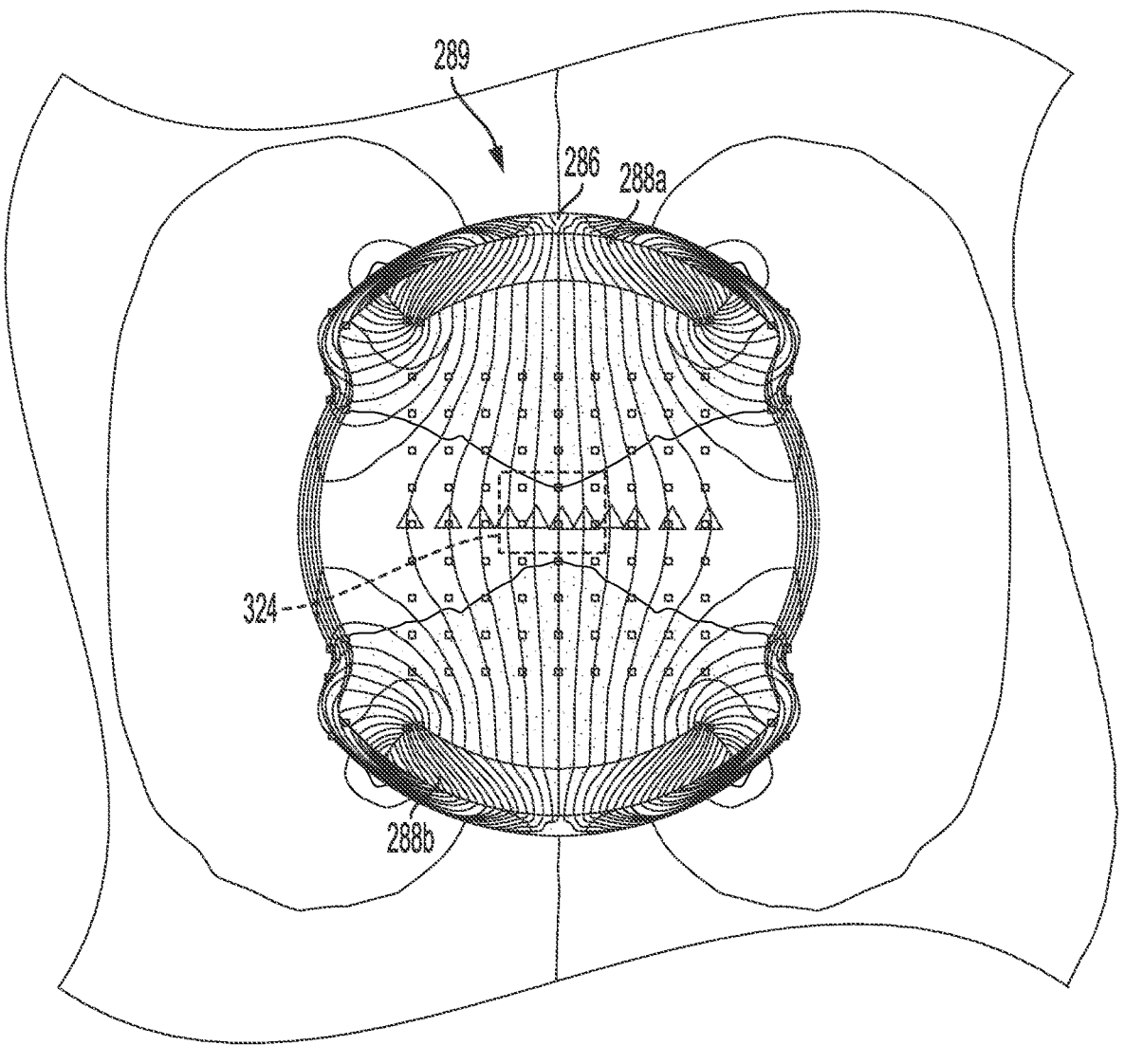
FIG. 10 illustrates a magnetic field generated by a magnetic field generator in accordance with another embodiment.

FIG. 10 illustrates a magnetic field generated by a magnetic field generator 289 in accordance with another embodiment. The arrangement of FIG. 10 corresponds to the embodiment of FIGS. 6 and 7. As shown in FIG. 10, a first magnet 288a and a second magnet 288b are spaced from one another. The magnets are arranged such that the magnetic field direction in the center between the two magnets 288a, 288b (e.g., in a channel of an elongated flexible body) is substantially unidirectional. As shown in FIG. 10, further from the center the magnetic field becomes less uniform and varies in direction. Accordingly, it may be desirable to position a magnetic field sensor 324 in the center between the first magnet 288a and the second magnet 288b where the magnetic field may remain substantially unidirectional to optimize the rotational orientation detection. In some embodiments, the magnetic field sensor 324 may be aligned with an axis of rotation of an instrument, which may be disposed in the center between the two magnets 288a, 288b. As shown in FIG. 10, a shield 286 that is disposed radially outwards from and extends around the first and second magnets 288a, 288b may assist in completing the magnetic circuit, strengthening the magnetic field, containing the magnetic field, and shaping the magnetic field in the center to be substantially unidirectional.

FIG. 11 illustrates a perspective view of tip cap 290 of a flexible elongate device 202, in accordance with embodiments of the present disclosure. As shown in FIG. 11, the tip cap 290 may include a plurality of orienting flats 292. The orienting flats 292 may be flats or another suitable shape configured to mate with corresponding mating flats of an instrument. The plurality of orienting flats 292 may be configured to restrict an instrument to a plurality of discrete rotational orientations. The number of discrete orientations may be based on the number of orienting flats 292. In some embodiments, the plurality of orienting flats 292 may be symmetrically disposed about a longitudinal axis of an elongated flexible body. For example, a hexagon shaped tip cap 290 including six orienting flats 292 may be able to receive and seat a hexagonal instrument housing in six discrete rotational orientations. As another example, a square shaped tip cap 290 including four orienting flats 292 may be able to receive and seat a square instrument in four discrete rotational orientations.

FIG. 12 illustrates a perspective view of an instrument housing 293 of an instrument 213, in accordance with embodiments of the present disclosure. As shown in FIG. 12, the instrument housing 293 includes a plurality of mating flats 294 that are configured to seat with the plurality of orienting flats 292 of the tip cap 290 of FIG. 11. The seating between the mating flats 294 and the orienting flats 292 may be configured to restrict the instrument 213 to a plurality of discrete rotational orientations. As shown in FIG. 12, the housing has an interior opening 291 which may be used to mount various components of the instrument. For example, a magnetic field sensor or magnetic field generator may be mounted in the opening 291. In the example where the instrument 213 is an imaging probe, a photosensitive detector and light source may be mounted in the opening 291. In some embodiments, an indentation 295 may be added to the mating region to allow saline to flow across the photosensitive detector. In some embodiments, the indentation 295 may replace one of the mating flats 294 such that there are fewer flats on the instrument housing 293 than there are orienting flats 292 on the tip cap 290.

FIG. 13 illustrates the tip cap 290 of FIG. 11 in use with the instrument housing 293 of FIG. 12. As shown in FIG. 13, the engagement between the orienting flats 292 of the tip cap 290 and the mating flats 294 of the instrument housing 293 results in the instrument being mated to tip cap 290. Once mated, the instrument is restricted to a discrete rotational orientation of a limited plurality of known possible orientations. Such an arrangement may eliminate certain error sources to increase confidence in orientation determination. Each mating flat 294 or orienting flat 292 may be associated with a range of sensed rotational angles about a longitudinal axis of the instrument and/or elongated flexible body. Accordingly, a magnetic field sensor may be employed to determine which of the plurality of discrete rotational orientations the instrument is in with respect to the distal tip by correlating the sensed magnetic orientation with a range of known magnetic orientations associated with each of the discrete orientations of the instrument when the orienting flats 292 are engaged with the mating flats 294. Thus, a reliable rotational orientation of the instrument may be determined based on magnetic field information. In some embodiments, the rotational orientation detection using magnetic field lines only needs to be sufficiently accurate and precise to differentiate between a limited number of possible mating orientations. The sources of the now filtered out error may include, but are not limited to mechanical tolerance between the camera's position with respect to the magnetic field sensor, sensor inaccuracy, lack of uniformity of the magnetic field where the magnetic field sensor can be positioned, mechanical tolerance between the magnets and the distal tip (or steer wires attached to the tip), noise in the magnetic field or data signals, magnetic field distortions, and the offset in magnetic field with respect to an intended direction of the magnet.

In some embodiments, an instrument and an elongated flexible body may include an odd number of mating flats 294 and orienting flats 292. Using an odd number of mating flats 294 and orienting flats 292 may help eliminate ambiguity in orientation determination caused by even number positions being symmetrical. Accordingly, determining a discrete position from an odd number of discrete positions may be beneficial in reliably determining a rotational orientation of an instrument. In some embodiments, seven mating flats 294 and orienting flats 292 may be employed.

Figure 14:
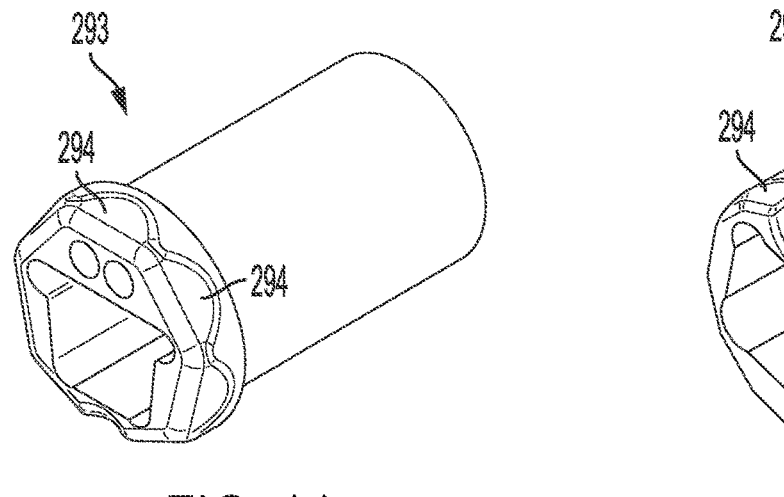
FIG. 14 illustrates another embodiment of an instrument housing for use with a flexible elongate device.

FIG. 14 illustrates another embodiment of an instrument housing 293 for use with a flexible elongate device. In the embodiment of FIG. 14, the instrument housing 293 includes seven mating flats 294. As discussed above, using an odd number of mating flats 294 may help eliminate ambiguity in orientation determination caused by even number positions being symmetrical.

Figure 15:
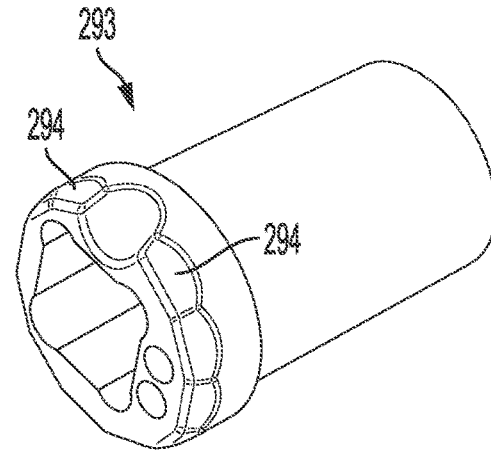
FIG. 15 illustrates another embodiment of an instrument housing for use with a flexible elongate device.

FIG. 15 illustrates another embodiment of an instrument housing 293 for use with a flexible elongate device. In the embodiment of FIG. 15, the instrument housing 293 includes twelve mating flats 294. In some cases, increasing the number of mating flats 294 may improve user friendliness as the available positions for the user is increased.

Figure 16:
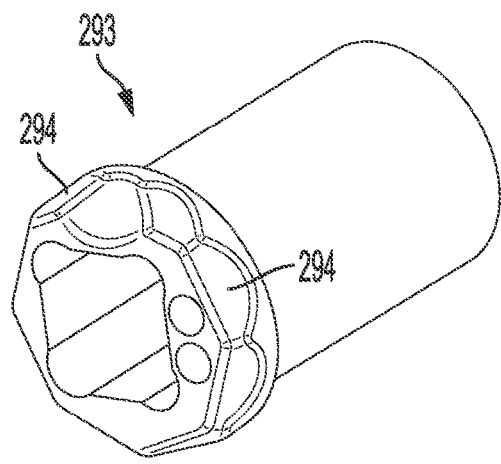
FIG. 16 illustrates another embodiment of an instrument housing for use with a flexible elongate device.

FIG. 16 illustrates another embodiment of an instrument housing 293 for use with a flexible elongate device. In the embodiment of FIG. 16, the instrument housing 293 includes eight mating flats 294.

For the sake of clarity, the various embodiments of a system including a magnetic field sensor and magnetic field generator have been described as being associated with a distal portion of the system. However, the disclosed systems may include a magnetic field sensor and corresponding magnetic field generator at any location along the corresponding lengths of an instrument and elongated flexible body the instrument is inserted into. Similarly, the mating and orienting flats associated with an instrument and corresponding portion of an elongated flexible body may also be located at any location along a length of the instrument and elongated flexible body.

FIG. 17 is a flow chart for an embodiment of operating a medical system comprising a flexible elongate device. In block 500, the method includes inserting an instrument into a channel of an elongated flexible body to align a magnetic field generator and a magnetic field sensor. In some embodiments, inserting the instrument into the channel may include seating the instrument in one of a plurality of discrete orientations about a longitudinal axis of the instrument. In some embodiments, alignment between a magnetic field generator and magnetic field sensor may be determined based on the proper seating of the instrument within the channel. For example, properly seating the instrument in the channel may automatically bring the magnetic field generator and magnetic field sensor into alignment with one another, with the magnetic field sensor being in a plane of the magnetic field lines generated by the magnetic field generator. In some embodiments, the instrument and elongated flexible body include structures (e.g., orienting and mating flats) that can mate as the instrument is advanced within the channel of the flexible elongate device, and without requiring a user to rotate the instrument or perform any rotational alignment to complete the mating. Once mated, the magnetic field sensor and the magnetic field generator are aligned.

In block 502, the method includes receiving sensor data from the magnetic field sensor regarding a magnetic field in the channel. In some embodiments, the sensor data may be received at a processor of a computer-assisted system. In some embodiments, the sensor data may define a direction of the detected magnetic field at one or more magnetic field sensors.

In block 504, the method includes determining an axial alignment of the magnetic field sensor with the magnetic field generator based on the sensor data. In some embodiments, such a determination may be based on the detection of a magnetic field strength above a threshold magnetic field strength. In some embodiments, one or more additional sensors may be employed at an offset along longitudinal axis L such that the magnetic field strength along the length of the flexible body may be compared in two or more locations to enhance the precision and accuracy of determining axial alignment. Arrangements for determining an axial position of an instrument relative to an elongated flexible body of a flexible elongate device are discussed further below with reference to exemplary FIGS. 18-21.

In block 506 of FIG. 17, the method includes determining a relative rotational orientation between the elongated flexible body including the channel and the instrument disposed in the channel. In some embodiments, such a determination may be based on a magnetic field direction within the channel. For example, based on the magnetic field direction, the orientation of the magnetic field sensor may be determined, from which the rotational orientation of the instrument may be determined. In another example, the rotational orientation of the instrument may be determined from the direction of the magnetic field. In some embodiments, the magnetic field sensor may be configured to provide information regarding magnetic field direction in the sensor data. In embodiments in which the instrument is restricted to a plurality of discrete orientations, each discrete orientation may be associated with a range of detected magnetic field directions. Accordingly, when a particular magnetic field direction is detected, a comparison to the plurality of separate ranges of magnetic field direction may be used to determine the discrete orientation the instrument is oriented in. For example, if a magnetic field direction of 45 degrees was sensed, the discrete orientation associated with a range of magnetic field directions, by virtue of being centered within the range, which includes the detected 45-degree magnetic field direction would be identified as the orientation of the instrument. Furthermore, the presence of the instrument within the channel or the proper placement of the instrument within the channel (e.g., instrument has been inserted to desired depth) may be determined based on the magnetic field sensor detecting the magnetic field.

FIG. 18 corresponds to the exemplary embodiment of FIGS. 4-5 and illustrates sensing positions 455 that one or more magnetic field sensors 324 may be positioned relative to first and second magnets 288*a*, 288*b* of a magnetic field generator 289 as instrument 213 passes through the flexible elongate device 202 along a longitudinal axis L of the flexible elongate device. FIG. 18 depicts vectors of the magnetic field generated by the first and second magnets 288*a*, 288*b*, at the sensing positions 455. The change in magnetic field vectors based on each of the sensing positions 455 for the magnetic field sensors may be employed by a processor to determine a longitudinal position of the magnetic field sensors relative to the first and second magnets 288*a*, 288*b*. In particular, the vectors associated with each sensing positions 455 may be indicative of a position and orientation of the magnetic field generated by the first and second magnets 288*a*, 288*b*. In the arrangement shown in FIG. 18, there may be ambiguity between the left and right side of the magnetic field generator 289 due to symmetry in the magnetic field vectors at the sensing positions 455. In some embodiments, such symmetry may be broken by using more than one magnetic field sensor positioned laterally offset relative to the longitudinal axis L such that every sensing position 455 has a unique combination of magnetic field vectors that are indicative of magnetic field position and orientation. The sensing positions 455 may be employed to achieve the determination of axial alignment of block 504 in FIG. 17, in some embodiments.

Figure 20:
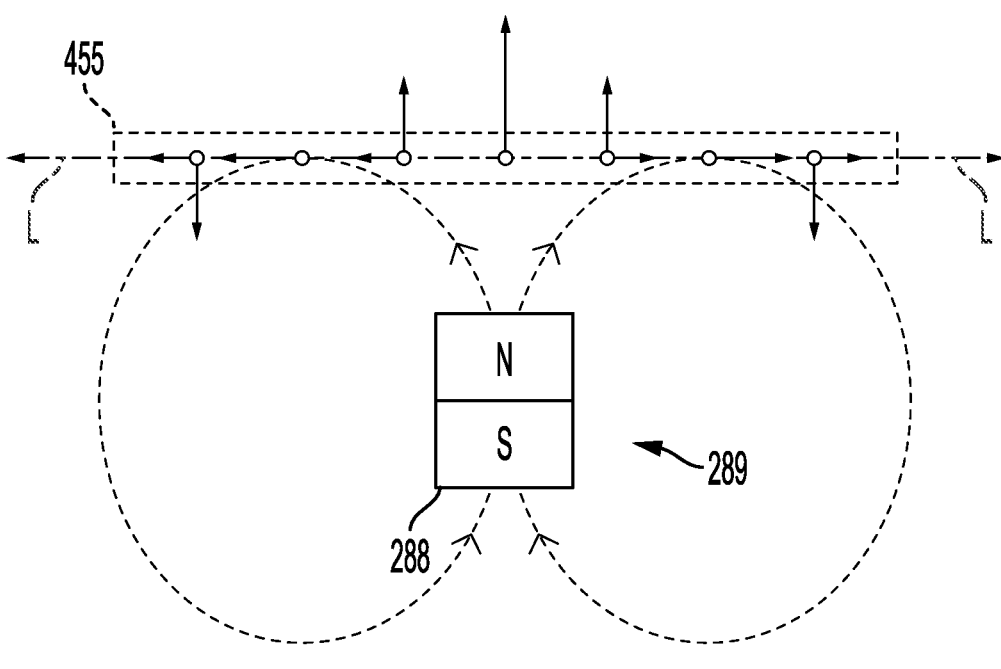
FIG. 20 illustrates a magnetic field generated by a magnetic field generator in accordance with another embodiment.
Figure 21:
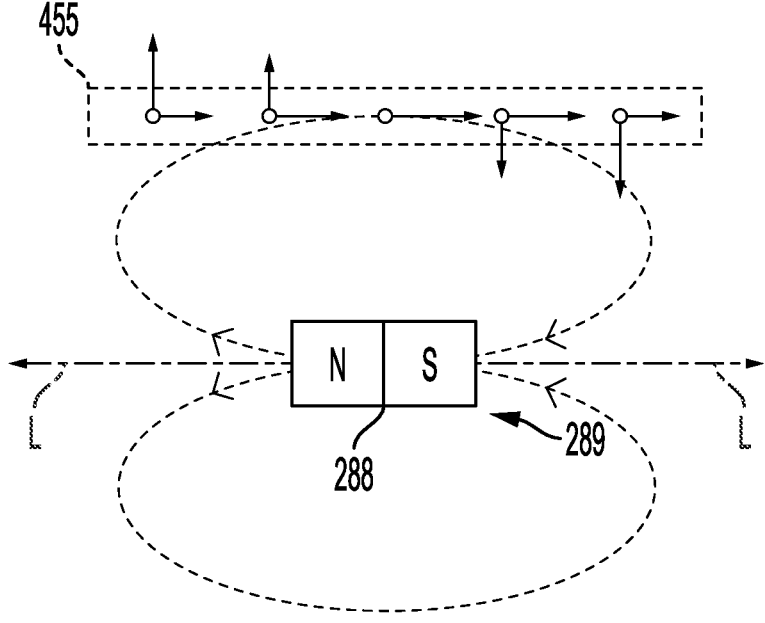
FIG. 21 illustrates a magnetic field generated by a magnetic field generator in accordance with another embodiment.

FIG. 19 depicts an alternative arrangement of a magnetic field generator 289 with first and second magnets 288*a*, 288*b* aligned in a direction parallel to the longitudinal axis L. As shown in FIG. 19, the sensing positions 455 disposed on the longitudinal axis L are each associated with a magnetic field vector. In the arrangement of FIG. 19, the alignment of the first and second magnets 288*a*, 288*b* is not as effective for sensing relative rotational orientation of a magnetic field sensor and magnetic field generator. In the arrangement shown in FIG. 19, there may be ambiguity between the left and right side of the magnetic field generator 289 due to symmetry in the magnetic field vectors at the sensing positions 455, similar to the arrangement of FIG. 18. In some embodiments, such symmetry may be broken by using more than one magnetic field sensor positioned laterally offset relative to the longitudinal axis L such that every sensing position 455 has a unique combination of magnetic field vectors that are indicative of magnetic field position and orientation. In some embodiments the arrangement shown in FIG. 19 may be employed to achieve the determination of axial alignment of block 504 in FIG. 17, in some embodiments FIGS. 20-21 depict similar scenarios to FIGS. 18-19, respectively. However, as in FIG. 9, the magnetic field generator 289 in these embodiments has only one magnet 288. In FIG. 20 the longitudinal axis L is aligned with sensing positions 455 for a magnetic field sensor. In other embodiments as shown in FIG. 21, the longitudinal axis L may instead be in line with the magnet 288 as in FIG. 21 in embodiments where a flexible elongate device 202 includes one or more magnetic field sensors and an instrument includes the magnet 288. As shown in FIGS. 20-21, the sensing positions 455 each includes vectors associated with the magnetic field generated by the magnet 288. The vectors may be employed to determine a rotational orientation of the magnetic field sensor relative to the magnet 288, as well as a longitudinal position of the magnetic field sensor relative to the magnet 288. In some embodiments, the magnetic field sensor may be a Hall effect sensor, in which case the determination of alignment or presence may be based on the activation of the Hall effect sensor. In some embodiments the arrangement shown in FIGS. 20-21 may be employed to achieve the determination of axial alignment of block 504 in FIG. 17, in some embodiments.

The above-described embodiments of the technology described herein can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semicustom or custom. As a specific example, some commercially available microprocessors have multiple cores such that one or a subset of those cores may constitute a processor. Though, a processor may be implemented using circuitry in any suitable format.

The terms "program" or "software" are used herein in a generic sense to refer to any type of computer code or set of computer-executable instructions that can be employed to program a computer or other processor to implement various aspects of the present disclosure as discussed above. Additionally, it should be appreciated that according to one aspect of this embodiment, one or more computer programs that when executed perform methods of the present disclosure need not reside on a single computer or processor but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the embodiments described herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Further, some actions are described as taken by a "operator." It should be appreciated that a "operator" need not be a single individual, and that in some embodiments, actions attributable to a "operator" may be performed by a team of individuals and/or an individual in combination with computer-assisted instruments or other mechanisms.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

The invention claimed is:

1. A medical system comprising:
an elongated flexible body including a channel extending through the elongated flexible body, wherein the elongated flexible body includes an articulable portion extending along at least a portion of a length of the elongated flexible body;
an instrument configured to be received in the channel of the elongated flexible body;
a magnetic field generator configured to generate a magnetic field;
a magnetic field sensor configured to detect the magnetic field generated by the magnetic field generator
wherein the magnetic field generator and the magnetic field sensor are in one selected from a group consisting of a first arrangement and a second arrangement,
wherein in the first arrangement, the magnetic field generator is attached to the elongated flexible body, and the magnetic field sensor is attached to the instrument, and
wherein in the second arrangement, the magnetic field generator is attached to the instrument, and the magnetic field sensor is attached to the elongated flexible body; and
a controller comprising at least one processor, the controller configured to:
receive sensor data from the magnetic field sensor, the sensor data indicative of the magnetic field generated by the magnetic field generator, and
based on the sensor data, determine a relative rotational orientation between the instrument within the channel and the elongated flexible body.

2. The medical system of claim 1, wherein the controller is configured to determine, based on the sensor data, presence of the instrument within the channel of the elongated flexible body.

3. The medical system of claim 1, wherein the controller is configured to determine, based on the sensor data, relative location of the instrument within the channel of the elongated flexible body along an axis of the instrument.

4. The medical system of claim 1, wherein, in the first arrangement, the magnetic field sensor is substantially aligned on a longitudinal axis of the instrument.

5. The medical system of claim 1, wherein the magnetic field generator includes a first magnet and a second magnet, the first magnet and the second magnet being disposed on opposing sides of the elongated flexible body about a longitudinal axis of the instrument.

6. The medical system of claim 1, wherein, in the first arrangement, rotation of the instrument with respect to the elongated flexible body causes the magnetic field sensor attached to the instrument to rotate with respect to the magnetic field generator attached to the elongated flexible body.

7. The medical system of claim 1, wherein, in the second arrangement, the magnetic field sensor includes a first sensor and a second sensor, the second sensor being positioned at a 90-degree offset about a longitudinal axis of the elongated flexible body from the first sensor.

8. The medical system of claim 1, wherein rotation of the instrument with respect to the elongated flexible body causes the magnetic field generator attached to the instrument to rotate with respect to the magnetic field sensor attached to the elongated flexible body.

9. The medical system of claim 1, wherein the elongated flexible body comprises a plurality of orienting flats, and wherein the instrument comprises a plurality of mating flats configured to engage the plurality of orienting flats to restrict the relative rotational orientation between the elongated flexible body and the instrument to a limited number of discrete orientations.

10. The medical system of claim 1, wherein the instrument is configured to mate with the elongated flexible body at a limited number of discrete rotational orientations, and wherein the controller is further configured to determine the relative rotational orientation between the instrument and the elongated flexible body based on correlating a detected direction of the magnetic field with one of the limited number of discrete rotational orientations.

11. The medical system of claim 1, wherein the sensor data includes magnetic field strength along at least two perpendicular axes, and wherein the controller associates different magnetic field strengths along the at least two perpendicular axes with different rotational orientations.

12. The medical system of claim 1, further comprising a ferromagnetic shield disposed around the magnetic field generator and the magnetic field sensor, wherein the ferromagnetic shield is configured to shape at least a portion of the magnetic field.

13. The medical system of claim 1, wherein the magnetic field sensor is a Hall effect sensor.

14. The medical system of claim 1, wherein the controller is configured to provide a display of an image captured by the instrument, the image being rotated in the display based on the relative rotational orientation.

15. A method of operating a medical system, the medical system comprising an elongated flexible body including a channel extending through the elongated flexible body, wherein the elongated flexible body includes an articulable portion extending along at least a portion of a length of the elongated flexible body, and an instrument configured to be received in the channel of the elongated flexible body, the method comprising:

receiving sensor data from a magnetic field sensor, the sensor data indicative of a magnetic field at the magnetic field sensor, wherein the magnetic field is generated by a magnetic field generator; and based on the sensor data, determining a relative rotational orientation between the elongated flexible body and the instrument within the channel, wherein the magnetic field generator and the magnetic field sensor are in one selected from a group consisting of a first arrangement and a second arrangement, wherein in the first arrangement, the magnetic field generator is attached to the elongated flexible body, and the magnetic field sensor is attached to the instrument, and wherein in the second arrangement, the magnetic field generator is attached to the instrument, and the magnetic field sensor is attached to the elongated flexible body.

16. The method of claim 15, further comprising at least one of:

determining based on the sensor data, presence of the instrument within the channel of the elongated flexible body, and determining, based on the sensor data, relative location of the instrument within the channel of the elongated flexible body along an axis of the instrument.

17. At least one non-transitory computer-readable medium comprising instructions thereon that, when executed by at least one processor associated with a medical system, the medical system comprising an elongated flexible body including a channel extending through the elongated flexible body, wherein the elongated flexible body includes an articulable portion extending along at least a portion of a length of the elongated flexible body, and an instrument configured to be received in the channel of the elongated flexible body, cause the medical system to:

receive sensor data from a magnetic field sensor, the sensor data indicative of a magnetic field at the magnetic field sensor, wherein the magnetic field is generated by a magnetic field generator; and based on the sensor data, determine a relative rotational orientation between the elongated flexible body and the instrument within the channel, wherein the magnetic field generator and the magnetic field sensor are in one selected from a group consisting of a first arrangement and a second arrangement, wherein in the first arrangement, the magnetic field generator is attached to the elongated flexible body, and the magnetic field sensor is attached to the instrument, and wherein in the second arrangement, the magnetic field generator is attached to the instrument, and the magnetic field sensor is attached to the elongated flexible body.

18. The at least one non-transitory computer-readable medium of claim 17, wherein the instructions further cause the medical system to perform at least one of:

determining based on the sensor data, presence of the instrument within the channel of the elongated flexible body, and determining, based on the sensor data, relative location of the instrument within the channel of the elongated flexible body along an axis of the instrument.

* * * * *